United States Patent
Musa et al.

(10) Patent No.: US 9,809,538 B2
(45) Date of Patent: Nov. 7, 2017

(54) RENEWABLE MODIFIED NATURAL COMPOUNDS

(75) Inventors: Osama M. Musa, Kinnelon, NJ (US); Ezat Khosravi, Gilesgate Moor (GB)

(73) Assignee: ISP INVESTMENTS LLC, Wilmington, DE (US)

( * ) Notice: Subject to any disclaimer, the term of this patent is extended or adjusted under 35 U.S.C. 154(b) by 977 days.

(21) Appl. No.: 13/811,561

(22) PCT Filed: Jul. 25, 2011

(86) PCT No.: PCT/US2011/045208
§ 371 (c)(1),
(2), (4) Date: Mar. 25, 2013

(87) PCT Pub. No.: WO2012/018588
PCT Pub. Date: Feb. 9, 2012

(65) Prior Publication Data
US 2013/0289284 A1 Oct. 31, 2013

Related U.S. Application Data

(60) Provisional application No. 61/367,614, filed on Jul. 26, 2010.

(51) Int. Cl.
| | |
|---|---|
| C07D 207/27 | (2006.01) |
| C08L 91/00 | (2006.01) |
| C07D 303/17 | (2006.01) |
| C07D 303/42 | (2006.01) |
| C09F 7/00 | (2006.01) |

(52) U.S. Cl.
CPC ......... *C07D 207/27* (2013.01); *C07D 303/17* (2013.01); *C07D 303/42* (2013.01); *C08L 91/00* (2013.01); *C09F 7/00* (2013.01)

(58) Field of Classification Search
CPC .................................................. C07D 207/27
See application file for complete search history.

(56) References Cited

U.S. PATENT DOCUMENTS

| | | | |
|---|---|---|---|
| 3,269,965 A * | 8/1966 | Johnson .............. | C08G 59/02 528/323 |
| 2003/0194386 A1 | 10/2003 | Bernard et al. | |
| 2006/0264524 A1 | 11/2006 | Abraham et al. | |
| 2007/0123673 A1 * | 5/2007 | Hofer .................. | C07D 207/27 526/264 |
| 2010/0166985 A1 | 7/2010 | Brockmeye et al. | |

OTHER PUBLICATIONS

Merriam-Webster, Definition for synthesis, obtained from http://www.merriam-webster.com/dictionary/synthesis on Mar. 18, 2016.*
Smith, Janice G. Organic Chemistry. 1st ed. New York, NY: McGraw-Hill, 2006, Chapter 7, pp. 221-269.*
Thompson et al. Polymer Journal 1995, 27, 325-338.*
Barluenga et al. Org. Lett. 2002, 4, 2817-2819.*
International Search Report, PCT/US2011/045208, published on Feb. 9, 2012.

* cited by examiner

*Primary Examiner* — Matthew Coughlin
(74) *Attorney, Agent, or Firm* — Thompson Hine LLP; William J. Davis

(57) ABSTRACT

Provided are modified natural compounds that are produced, at least in part, from (A) at least one epoxidized and/or maleated natural fatty acid, or epoxidized and/or maleated natural oil, and (B) at least one lactam having at least one hydroxyl functional group, wherein the lactam may be in a blend with one or more optional alcohol(s). Among other properties, the modified natural compounds may exhibit dispersibility or solubility characteristics in water and/or alcohols. The invention further provides a wide variety of compositions comprising the modified natural compounds.

18 Claims, No Drawings

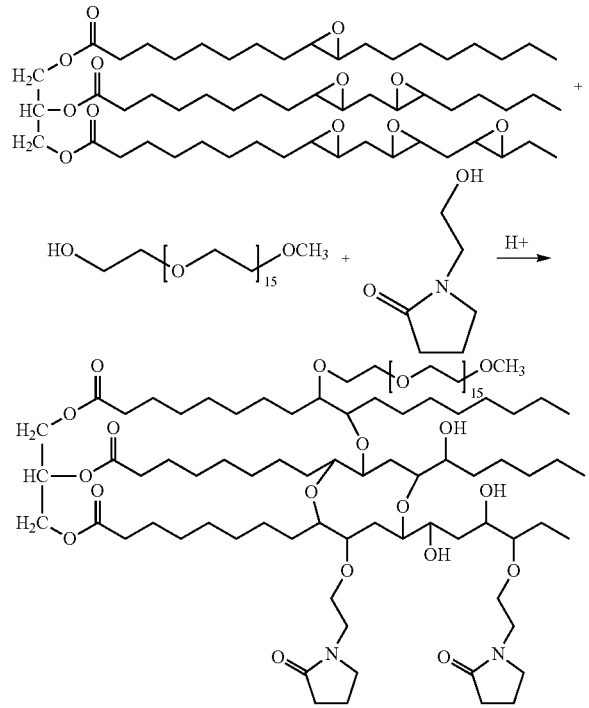

RENEWABLE MODIFIED NATURAL COMPOUNDS

BACKGROUND OF THE INVENTION

Field of the Invention

Provided are renewable modified fatty acids and modified natural oils derived from natural fatty acids and natural oils. These modified compounds may exhibit properties that differ from the natural starting material, e.g., solubility in various solvents, softening/liquid points, miscibility, flexibility, glass transition temperature, and/or solubilization potential.

The modified fatty acids and modified natural oils can be incorporated into a wide variety of compositions. Such compositions include, but are not limited to personal care (e.g., hair care, sun care, skin care, oral care), adhesives, coatings, paints, electronics, Household, Industrial and Institutional (HI&I) compositions, inks, membranes, metal working fluids, oilfield chemicals, plastics and plasticizers, textiles, industrial products, biocides, pharmaceuticals/nutritionals, and agrochemical compositions.

Description of Related Art

Natural fatty acids, such as palmitate, stearate, oleate, linoleanate, and linoleate, and natural oils, such as soybean and linseed oils, are one of the most promising raw materials for the synthesis of renewable compounds, including polymers, plastics, and plasticizers. These natural materials are inexpensive, highly abundant, come from reliable and sustainable sources, and have high potential for modification. Natural oils are generally blends of different triglycerides, the esterification product of fatty acids and glycerol, and contain varying degrees of unsaturation (i.e., double bonds). Oils can be characterized by a hydroxyl value and the fatty acid compositions. Both natural fatty acids and natural oils must be chemically modified to make them sufficiently reactive to allow structural alterations and polymerizations to occur because the olefin functional groups are relatively unreactive. Unsaturated double bonds in this compounds have been converted to epoxide functional groups and succinic anhydride functional groups, allowing the addition of many hydroxyl containing species to be introduced into the natural oils. Examples of such epoxidized natural oils and the products derived from the epoxides are disclosed in U.S. Pat. Nos. 3,066,159; 5,973,082; and 7,691,914. 4,244,829; 4,886,893; 4,962,179; 5,232,968; 6,890,967; as well as E.P. patents 437,001; 981,321; 1,117,377; 1,338,630; 1,813,311; and G.B. patents 772,151 and 825,691. Each of these patents is incorporated in its entirety by reference. These fatty acids provide functionality in many different types of products, ranging from lubricating oils, printing inks, agricultural treatments, coatings, personal care compositions, emollients, detergents/soaps, and plasticizers.

Epoxidized and maleated natural oils are natural oils that have been chemically functionalized by the chemical addition of epoxide (oxirane) and succinic anhydride functional groups. Examples include epoxidized and maleated soybean oil and linseed oil, although, as will be discussed later, unsaturated natural oils lend themselves to these chemical functionalizations. Epoxidized soybean oil (ESO), which is environmentally friendly, renewable, and biodegradable, finds use as a plasticizer for polymer, for improving polymer mechanical strength, and in formulating inks, coatings, and lubricants. In addition, ESO and a related compound, maleated soybean, are both known to the personal care industry.

A discussion of epoxidized rapeseed oil modified by alcohols of varying chain lengths is provided in the article "Modification of rapeseed oil and its lubricating characteristics," by Q. H. Li and D. H. Tao, published in *J. Shanghai Jiaotong Univ.*, 43, 12, Dec.2009, p. 1953.

Other disclosures of related compounds include U.S. Pat. Nos. 3,066,159; 6,057,375; and 7,691,914. Each of the U.S., E.P., and G.P. patents and the journal article cited above are hereby incorporated its entirety by reference.

Despite the renewability, biodegradability, sustainability, and beneficial functions provided by natural fatty acids, natural oils and their epoxidized/maleated counterparts, they exhibit properties that can limit their application. For example, both ESO and maleated soybean oil are insoluble and non-dispersible in water or alcohols. As a result, these fatty acids and oils may tend to exude or phase-separate from formulated compositions. This feature makes their formulation more difficult, often requiring additional ingredients to facilitate solutions, emulsions, or dispersions. Natural and epoxidized/maleated natural oils may not impart the desired property needed in end-uses, such as solubilization capability, glass transition, flexibility, shine, and/or plasticization. Consequently, the performance (including, but not limited to stability, resistance to phase separation, absorption, clean-up, solubility potential, staining potential, lubrication, film formation, uniformity of spreading, comedogenic tendency, ease of removal), and aesthetic qualities (such as skin-feel, greasiness, shiny appearance) may be less than desired. Finally, although such fatty acids and oils are an important renewable material, they are not always the formulator's first choice, and, in fact, often are not considered at all.

Accordingly, there is a need for materials that are renewable, natural, and biodegradable having different and controllable chemical, physical, and/or mechanical properties such that the limitations found in natural and epoxidized/maleated natural oils are minimized or eliminated.

SUMMARY OF THE INVENTION

The invention provides for modified natural compounds that overcome these limitations, wherein the modified compounds are produced from the reaction of: (A) at least one epoxidized and/or maleated natural fatty acid, epoxidized and/or maleated natural oil, or blend thereof, and (B) at least one lactam having at least one hydroxyl functional group, wherein the lactam may be in a blend with one or more optional alcohol(s). The "lactam having at least one hydroxyl functional group" has the structure:

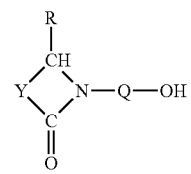

wherein Y is an alkylene or alkenylene group comprising 2 to 50 carbon atoms, wherein 2 to 4 carbon atoms reside in the lactam ring between the

group and the

group;

Q is selected from the group consisting of functionalized and unfunctionalized alkylene of linear, branched, or cyclic structure, arylene, and combinations thereof, wherein any of the beforementioned groups may be with or without oxygen atom(s); and R is selected from the group consisting of hydrogen, functionalized and unfunctionalized cycloalkyl, alkenyl, and aryl groups, wherein any of the groups may be with or without heteroatoms.

The invention also embraces a wide variety of compositions having the above-modified natural compounds including adhesives, agricultural compositions, beverage compositions, cleaning and detergent compositions, coatings, foods, printing compositions, membrane formulations, oilfield formulations, personal care compositions (e.g., hair care, hair styling, skin care, oral care, sun care, color cosmetic, and including but not limited to moisturizing, anti-wrinkle, and sunscreen compositions), pharmaceutical/nutritional compositions, pigment dispersions, emulsifiers, solubilizers, stabilizers, and carrier systems.

DETAILED DESCRIPTION

Provided are modified natural compounds that offer unique capabilities for molecule customization in order to achieve wide-ranging chemical, physical, and mechanical properties. Due in part to these customizations, the modified compounds provide formulators with extended opportunities to improve existing compositions of the known art field, as well as to create entirely new products so that these important renewable materials can be used.

Before providing yet more details about the modified compounds and how they find application, it is useful to setforth the meaning of several terms:

The term "heteroatom" refers to atoms such as oxygen, nitrogen, sulfur, and phosphorous.

The term (meth)acrylate includes both acrylate and methacrylate.

The term "natural fatty acid" refers to any number of compounding comprising a carboxylic acid functional group and a aliphatic chain, which may be saturated or unsaturated. The many variations in fatty acids occur due to the aliphatic chain length, the number and position of unsaturated carbon-carbon bonds along the chain, and the cis/trans configuration of the chain. Fatty acids may be categorized as short-chain (meaning the chain comprises less than 6 carbon atoms), medium-chain (6-12 carbon atoms in the chain), long-chain (more than 12 carbon atoms in the chain), or as very long-chain (more than 22 carbon atoms in the chain). Examples of fatty acids include the following compounds: myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, as well as lauric acid, myristic acid, palmitic acid, stearic acid, arachidic acid, behenic acid, lignoceric acid, and cerotic acid. To be epoxidized and/or maleated, the natural fatty acid has at least one unsaturated carbon-carbon bond, which may be produced by dehydrogenation.

The term "natural oil" refers to compounds comprising triglycerides and may contain varying levels of fatty acids, monoglycerides, and diglycerides. Triglycerides result from the esterification of one or more fatty acids with glycerol. Thus, triglycerides may be considered to be alkyl and/or alkenyl esters of glycerol. One non-limiting example of a natural oil is soybean oil, which is a blend of the esterification products of glycerol with five fatty acids: palmitate, stearate, oleate, linoleanate, and linoleate. For example, natural soybean oil may be represented by the structure:

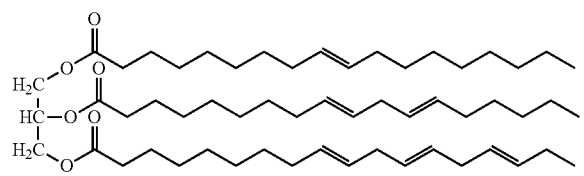 [SMILES: CC/C=C/C/C=C/C/C=C/CCCCCCCC(=O)OCC(COC(=O)CCCCCCC/C=C/CCCCCCCC)OC(=O)CCCCCCC/C=C/C/C=C/CCCCC]

Triglycerides having a high degree of unsaturation (such as those based on α-linolenic acid, arachidonic acid, eicosapentanoic acid, and docosahexaenoic acid) offer multiple reactive sites for adding epoxidized and/or succinic anhydride functional groups (discussed later).

Other, non-limiting examples of natural oils include avocado, coconut, corn, cottonseed, jojoba, linseed, nut, olive, palm, raisin, rapeseed, safflower, sesame, soybean, squash, sunflowers oils, and mixtures thereof. Of course, yet more natural oils exist and are fully embraced by the invention.

The term "personal care composition" refers to a composition intended for use on or in the human body and may be an oral care composition, a hair care composition, a hair styling composition, a face care composition, a lip care composition, an eye care composition, a foot care composition, a nail care composition, a sun care composition, a deodorant composition, an antiperspirant composition, a cosmetic composition (including color cosmetics), a skin cleaning composition, an insect repellant composition, a shaving composition, a toothpaste, a mouthwash, a tooth whitener, a tooth stain remover, and/or a hygiene composition. Among their many uses, hair care and hair styling compositions find application in enhancing hair shine, cleansing hair, conditioning hair, repairing split ends, enhancing hair manageability, modulating hair stylability, protecting hair from thermal damage, imparting humidity resistance to hair and hair styles, promoting hair style durability, changing the hair color, straightening and/or relaxing hair, and/or providing protection from UV-A and/or UV-B radiation. Other personal care compositions, such as those for skin care and sun care compositions, are useful for protecting from UV-A and/or UV-B radiation, imparting water resistance or water proofness, moisturizing skin, decreasing and/or minimizing the appearance of wrinkles, firming skin, decreasing or minimizing the appearance of skin blemishes (such as lentigo, skin discolorations, pimples, or acne), changing skin color (such as color cosmetics for the face, cheeks, eyelids, or eye lashes). Oral care compositions according to the invention may be used as denture adhesives, toothpastes, mouthwashes, tooth whiteners, and/or stain removers. Personal care compositions also are used for delivering an active (such as to the skin, hair, or oral cavity).

Modified Natural Fatty Acids and Modified Natural Oils

As mentioned above, the invention provides a wide variety of modified compounds that can result from the reaction of: (A) at least one epoxidized natural fatty acid, maleated natural fatty acid, epoxidized natural oil, maleated natural oil, or blend thereof, and (B) at least one lactam having at least one hydroxyl functional group, wherein the lactam may be in a blend with one or more optional alcohol(s). The "lactam having at least one hydroxyl functional group" may be represented by the structure:

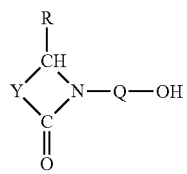

wherein:

Y is an alkylene or alkenylene group comprising 2 to 50 carbon atoms, wherein 2 to 4 carbon atoms reside in the ham ring between the

group and the

group;

Q is selected from the group consisting of functionalized and unfunctionalized alkylene of linear, branched, or cyclic structure, arylene, and combinations thereof, wherein any of the beforementioned groups may be with or without oxygen atom(s); and R is selected from the group consisting of hydrogen, functionalized and unfunctionalized alkyl, cycloalkyl, alkenyl, and aryl groups, wherein any of the groups may be with or without heteroatoms.

Regarding reactant (A), it is appreciated that epoxidized (or maleated) natural oils may comprise an amount of free fatty acids (i.e., not esterified with glycerol), and that the reactive nature of these free fatty acids is essentially the same as the individual chains comprising the triglyceride (i.e., fatty acids esterified with glycol). Equally relevant, the (A) reactant may consist essentially only of epoxidized (or maleated) fatty acids but not a natural oil. For example, the fatty acids may be the hydrolysis reaction product of the triglycerides that constitute natural oils. Given the fundamental and interrelated nature of nature fatty acids and nature oils, the invention embraces both materials as the (A) reactant, and consequently, the modified natural compounds thus produced.

For example, reactant (A) may be an epoxidized natural fatty acid or natural oil, which is a natural fatty acid or natural oil wherein one or more double bonds has/have been converted to epoxide functional group(s). An illustrative example of one type of epoxidized natural oil may be represented by the structure:

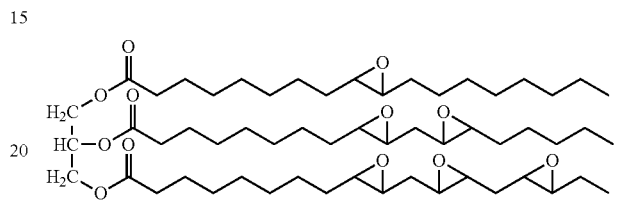

One commercial route for producing epoxidized natural oil is the reaction of a natural oil with an oxidizer, such as peroxyacid. There are other reactive routes for preparing epoxides.

Many different epoxidized natural oils are known, including the epoxidized natural oils taught in U.S. Pat. Nos. 3,236,795; 4,215,058;

Commercial epoxidized natural oils offered for sale include the following products: the Vikoflex® product line (Vikoflex® 4050, 5075, 7170, 7190) by Arkema Inc. (King of Prussia, Pa.); Epoxol 9-5 Epoxidized Linseed Oil by American Chemical Service Inc. (Griffith, Ind.); and the epoxidized soybean oils of The Hallstar Company (Chicago, Ill.) which include Paraplex® G-60 a high molecular weight soybean oil epoxide, acid value of 0.3 mg KOH/g, and 5.5% epoxide oxygen content) and Paraplex® G-62 (a high molecular weight soybean oil epoxide, acid value of 0.11 mg KOH/g, and 6.8% epoxide oxygen content), as well as Suprmix® Paraplex® G-62 (a high molecular weight epoxidized soybean oil dispersed on an amorphous silica carrier).

One or more epoxidized natural fatty acid(s) and/or epoxidized natural oil(s) may be reacted with reactant (B), which is at least one lactam having at least one hydroxyl function group, or a blend of the lactam with one or more optional alcohol(s). For simplicity, the (B) reactant can be represented by R'OH, wherein R' represents the non-hydroxyl residue of the hydroxyl-containing lactam and/or of the alcohol. If one assumed that all epoxide functional groups are fully reacted, then the reaction scheme involving an epoxidized natural oil may be represented as set out below:

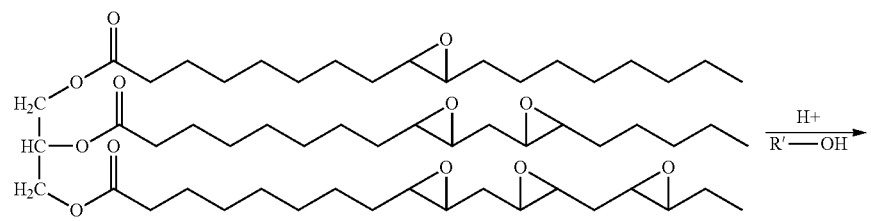

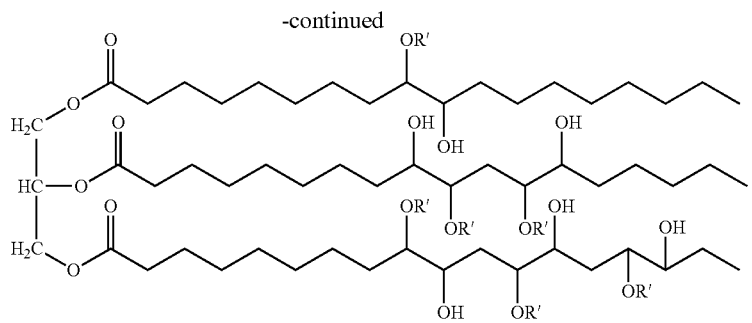

Of course, not all epoxide functional groups need be reacted, in which case the modified natural compound (i.e., the reaction product) may contain closed epoxide functional groups, which may optionally be reacted with yet other reactive chemistries.

The epoxidized natural fatty acid and/or epoxidized natural oil also may comprise other functional groups and need not comprise only epoxide functional groups.

Alternatively, or in combination with one or more epoxidized natural oils, the reactant (A) may be a maleated natural fatty acid and/or a maleated natural oil. The terms "maleated natural fatty acid" and "maleated natural oil" refers to a natural fatty acid or natural oil wherein one or more double bond(s) have been reacted with maleic anhydride to form a succinic anhydride-containing counterpart. U.S. Pat. No. 7,361,710 describes non-limiting methods for making such maleated natural oils, and one preparation scheme to prepare a maleated natural oil may be represented as follows:

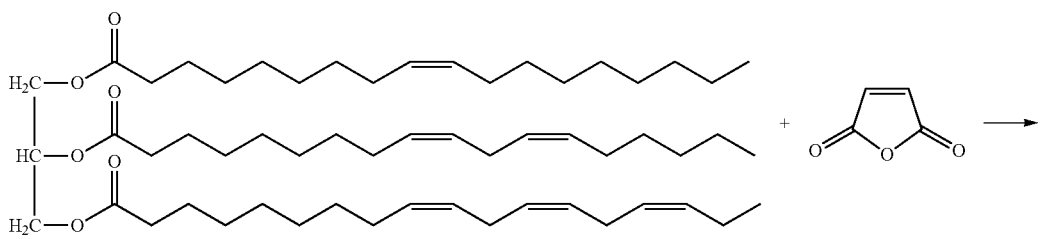

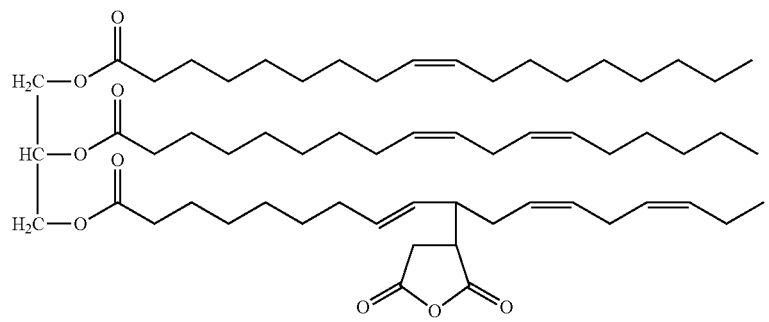

Of course, the ene reaction can occur at a different unsaturated carbon-carbon bond, as well as at unsaturated carbon-carbon bonds within the same molecule. Also, other routes of synthesis are known, and yield suitable maleated natural oils for use with the invention.

Maleated natural oils are generally well known, and include the compounds taught in U.S. Pat. Nos. 3,428,589 and 7,361,710, which are incorporated in their entirety by reference. Additional disclosure related to anhydride-functionalized vegetable oils is provided by Aydin, S., et al., *Prog Org Coat,* 51, 273-279, 2004; and by Guner, F. S., et al., *Prog Polym Sci,* 31, 633-670, 2006, which are incorporated in their entirety by reference. Any natural oil that is not completely saturated can be maleated, and these oils include: avocado, coconut, corn, cottonseed, jojoba, linseed, nut, olive, palm, raisin, rapeseed, safflower, sesame, soybean, squash, sunflowers oil. Of course, blends of these oils may be used. Modified natural oils made from a maleated natural oil reacted with water to form its half-ester form, or with one or more hydroxide(s) to form the corresponding salt form. These reactions may be represented by the chemical reaction schemes:

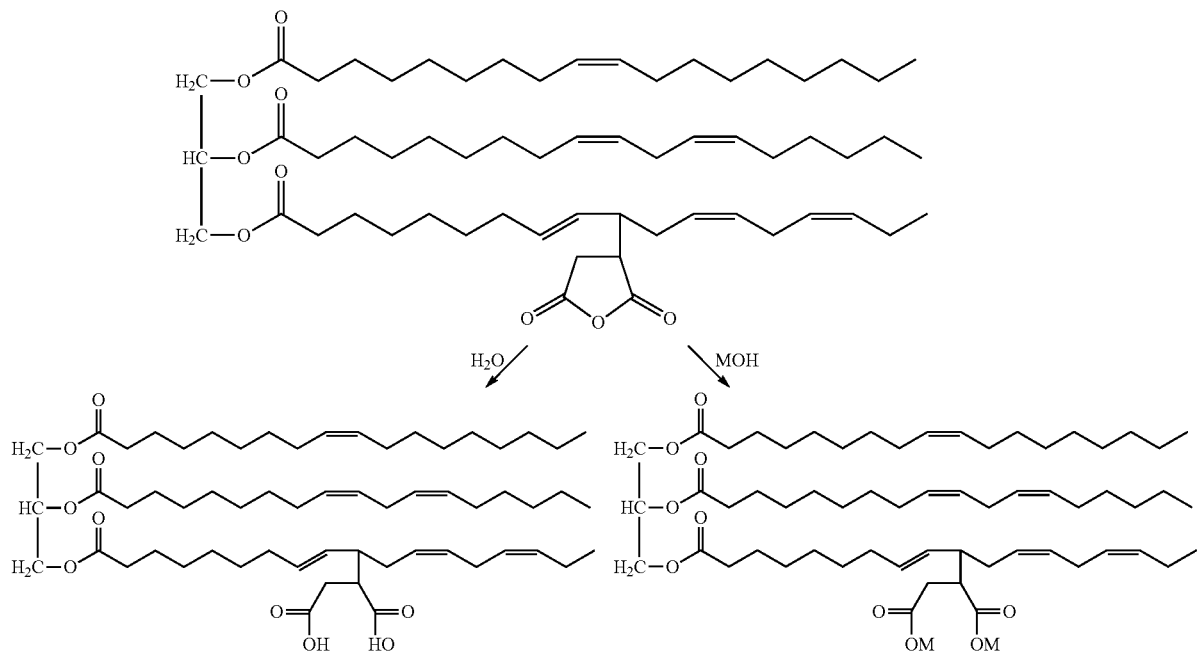

wherein chemical group M refers to hydrogen or an alkali metal or an alkaline earth metal, which include lithium, sodium, potassium, rubidium, caesium, and francium, and beryllium, magnesium, calcium, strontium, barium, and radium. In various, non-limiting embodiments M is magnesium, calcium, or combinations thereof.

The maleated natural fatty acid and/or maleated natural oil also may comprise other functional groups and need not comprise only succinic anhydride functional groups.

As set out above, the modified compounds are renewable and have chemical, physical, and/or mechanical properties useful in a wide variety of compositions. For example, unlike naturals oil, some of the modified natural oils may be dispersible or soluble in water and/or alcohols, making them easier to formulate in the wide variety of compositions.

In addition to the (A) reactant, the modified natural compounds are also synthesized from at least one (B) reactant, which is a lactam having at least one hydroxyl functional group, or from a blend of such a lactam with one or more alcohols. The "lactam that has at least one hydroxyl functional group" may be represented by the structure:

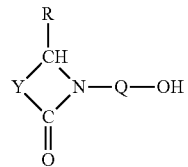

wherein:

Y is an alkylene or alkenylene group comprising 2 to 50 carbon atoms, wherein 2 to 4 carbon atoms reside in the lactam ring between the

group and the

group;

Q is selected from the group consisting of functionalized and unfunctionalized alkylene of linear, branched, or cyclic structure, arylene, and combinations thereof, wherein any of the beforementioned groups may be with or without oxygen atom(s); and R is selected from the group consisting of hydrogen, functionalized and unfunctionalized alkyl, cycloalkyl, alkenyl, and aryl groups, wherein any of the groups may be with or without heteroatoms.

Together with at least one (A) reactant, the many choices available for the (B) reactant(s) offer the scientist a multitude of possibilities to impart a wide range of final properties to the modified natural oil. With the proper selection of the (A) reactant, and the Y, Q, and R groups, modified natural compounds with a wide variety of hydrophilic-to-hydrophobic balance, even within one molecule, can be prepared. Such functionality can improve the performance of the modified natural compound, especially with regard to various chemical, physical, and/or mechanical properties, such as solubility, dispersibility, glass transition temperature, flexibility, miscibility with other ingredients, and/or solubilization potential for active ingredients in the intended application areas.

In different embodiments, the —Y— group present in the lactam ring between the

group and the

group may be

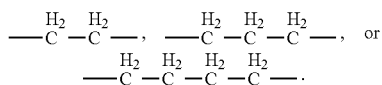

The lactam rings formed are pyrrolidone, piperidone, and caprolactam, respectively. In one particular embodiment, the —Y— groups are

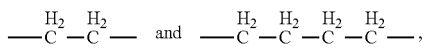

resulting in the respective structures:

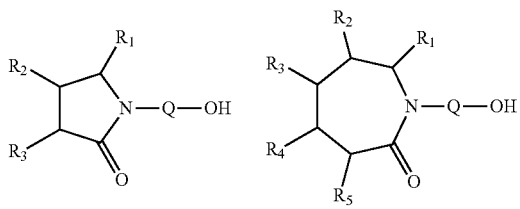

wherein $R_1$, $R_2$, $R_3$, $R_4$, and $R_5$ are independently selected from the group consisting of hydrogen, functionalized and unfunctionalized alkyl, cycloalkyl, alkenyl, and aryl groups, wherein any of the groups may be with or without heteroatoms. $R_1$ through $R_5$ in the above structures have the same definition as R in the generalized structure for reactant (B) provided earlier.

Independent of the choice of the —Y— group, Q may be a functionalized or unfunctionalized alkylene having 1-10 carbon atoms of linear, branched, or cyclic structure, arylene, and combinations thereof, wherein any of the beforementioned groups may be with or without oxygen atom(s). More particularly, Q comprises 1-6 carbon atoms.

In yet other examples, each of $R_1$, $R_2$, $R_3$, $R_4$, and $R_5$ may be hydrogen, or functionalized and unfunctionalized alkyl, cycloalkyl, alkenyl, and aryl groups containing 1-10 carbon atoms, wherein any of the groups may be with or without heteroatoms. Most particularly, $R_1$, $R_2$, $R_3$, $R_4$, and $R_5$ are hydrogen and the "lactam that has at least one hydroxyl group" has a structure represented by:

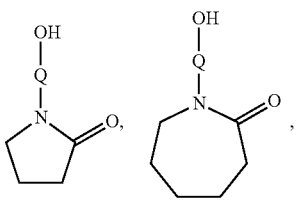

or blends thereof.

When the Q group is ethylene in the first of the hydroxy lactams illustrated above, then the lactam is hydroxyethyl pyrrolidone, i.e.:

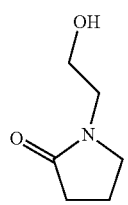

which is also known as N-2-hydroxyethyl-2-pyrrolidone. This compound is offered into commercial sale under the trade name HEP° by International Specialty Products (Wayne, N.J.).

Of course, it is a trivial matter for one of ordinary skill in the art to employ any of the numerous web-based chemistry tools (such as emolecules.com, reaxys.com, or the PubChem Compound search of the National Center for Biotechnology Information/U.S. National Institutes of Health) in order to identify other hydroxy lactams that meet the specification setforth above.

As described above, the (B) reactant may be a "lactam that has at least one hydroxyl group," or may be a blend of at least one such lactam with one or more alcohols. The alcohol may be any monohydric alcohol, any polyhydric alcohol, any unsaturated aliphatic alcohol, and/or any alicyclic alcohol. Blends of these various alcohols may be employed.

Non-limiting examples of monohydric alcohols include: methanol, ethanol, 1-propanol, 2-propanol, 1-butanol, 2-butanol, as well as higher molecular weight monohydric alcohols like amyl alcohol, cetyl alcohol, and benzyl alcohol.

Additional families of monohydric alcohols include polyethylene glycol alkyl ethers of all molecular weight, such as polyethylene glycol methyl ether having any number of ethylene oxide repeating units.

More examples of monohydric alcohols are monomers having one hydroxyl functional group. These hydroxyl-containing monomers can be selected from any of the following monomer families: maleic anhydrides, maleic acids, maleimides, maleates, fumarates, vinyl amides, vinyl esters, vinyl acetates, (meth)acrylates, (meth)acrylamides, styrenes, cinnamyls, vinyl imidazoles, vinyl pyridines, vinyl lactams, vinyl sulfones, vinyl carbonates, vinyl carbamates, vinyl ureas, vinyl thiocarbamates, vinyl silanes, vinyl siloxanes, vinyl acetamides, allyl compounds, and vinyl ethers. A non-limiting example is the family of the hydroxyl-containing (meth)acrylate monomer, such as, but are not limited to hydroxyalkyl (meth)acrylate, which includes hydroxymethyl (meth)acrylate and hydroxyethyl (meth)acrylate and others. Other hydroxy-containing monomers also can be used.

Polyhydric alcohols are those alcohols that have more than one hydroxyl functional group, and include the diol and sugar alcohol subfamilies. Specific and non-limiting examples of polyhydric alcohols are ethylene glycol, polyethylene glycols (of all molecular weights), propylene glycol, polypropylene glycols (of all molecular weights), 1,3-propanediol, 1,4-butane diol, 1,5-pentanediol, 1,6-hexanediol, methoxypolyethylene glycols, glycerin, erythritol, mannitol, and xylitol, monosaccharides, glucose, polysaccharides, starch, cellulose, hydroxyethylcellulose, hydroxypropylcellulose, cyclodextrins, glyco-proteins, polymeric alcohols, polyvinyl alcohol, and the like.

Examples of hydroxyethylcellulose include the various grades of Natrosol™ HEC, and PolySurf™ (Ashland Inc.; Wilmington, Del.).

Examples of hydroxypropylmethylcellulose (hypromellose) include the various grades of Benecel™ HPMC (Ashland Inc.; Wilmington, Del.); and the various grades of Methocel™ (The Dow Chemical Company; Midland, Mich.).

Examples of hydroxypropylcelluloses include the various grades of Klucel, PrimaFlor™, and AeroWhip HPC (Ashland Inc.; Wilmington, Del.).

Examples of cyclodextrins include α-cyclodextrins, such as Cavamax® W6 Pharma; β-cyclodextrins, such as Cavamax® W7 Pharma; γ-cyclodextrins, such as Cavamax® W8 Pharma; hydroxypropyl-β-cyclodextrins, such as Cavasol® W7 HP Pharma, Cavitron® W7 HP5 Pharma, and Cavitron® W7 HP7 Pharma, all marketed by ISP (Wayne, N.J.).

Also suitable are the various grade of guar hydroxypropyltrimonium chloride, including the various grades of N-Hance™ Cationic Guar and AquaCat™ Cationic Guar Solutions (Ashland Inc.; Wilmington, Del.). Also suitable are the methylhydroxyethylcellulose and methylhydroxypropylcellulose chemistries, such as the Cuminal® products of Ashland Inc.

Additional examples of polyhydric alcohols are polyhydric hydroxyl-containing monomers. These monomers resemble those mentioned as monohydric monomers (above), except they contain more than one hydroxyl group. Again, these monomers can be selected from any of the following monomer families: maleic anhydrides, maleic acids, maleimides, maleates, fumarates, vinyl amides, vinyl esters, vinyl acetates, (meth)acrylates, (meth)acrylamides, styrenes, cinnamyls, vinyl imidazoles, vinyl pyridines, vinyl lactams, vinyl sulfones, vinyl carbonates, vinyl carbamates, vinyl ureas, vinyl thiocarbamates, vinyl silanes, vinyl siloxanes, vinyl acetamides, allyl compounds, and vinyl ethers.

An example of polyhydric monomers include 2,3-dihydroxypropyl (meth)acrylate. One skilled in the art can recognize other monomers having more than 1 hydroxyl functional group that can be used.

Other polyhydric alcohols are all polymers polymerized from monomers having one or more hydroxyl functional groups. These monomers can be selected from any of the following monomer families: maleic anhydrides, maleic acids, maleimides, maleates, fumarates, vinyl amides, vinyl esters, vinyl acetates, (meth)acrylates, (meth)acrylamides, styrenes, cinnamyls, vinyl imidazoles, vinyl pyridines, vinyl lactams, vinyl sulfones, vinyl carbonates, vinyl carbamates, vinyl ureas, vinyl thiocarbamates, vinyl silanes, vinyl siloxanes, vinyl acetamides, allyl compounds, and vinyl ethers. Non-limiting examples are the polymers polymerized from hydroxyl-containing (meth)acrylate monomers, such as, but are not limited to hydroxyalkyl (meth)acrylate, which includes hydroxymethyl (meth)acrylate and hydroxyethyl (meth)acrylate and others. Of course, the polyhydric alcohol can be produced by polymerizing other monomers having one or more hydroxyl functional group(s).

(monohydric and/or polyhydric) hydroxyl-containing monomers. These polymers include those polymerized from the hydroxyalkyl (meth)acrylates, such as hydroxymethyl (meth)acrylates, hydroxyethyl (meth)acrylates, and related hydroxyalkyl (meth)acrylates. Other polymers polymerized from A review of the alcohol types shows they also can be unsaturated aliphatic alcohols, which are those alcohols with one or more unsaturated carbon-carbon bonds, like allyl alcohol, geraniol, and propargyl alcohol. These alcohols offer the carbon-carbon double bond functionality for further reactive chemistries, such as crosslinking (e.g., for inks or coatings).

Finally, alicyclic alcohols may be included along with the (B) lactam. One skilled in the art recognizes that alicyclic alcohols are aliphatic ring alcohols. Non-limiting examples of alicyclic alcohols include inositol and menthol.

Numerous benefits can be achieved by the inclusion of one or more alcohols together with the lactam that has at least one hydroxyl group. For example, water and/or alcohol solubility of the reaction product (i.e., the modified natural compound) can be affected by selecting alcohol(s) of low or high molecular weight, and the addition level of the alcohol(s). Additionally, incorporating an alcohol(s) into the modified natural compound can alter its solubilization capability, for example, wherein specific functionalities (i.e., ring structures, ethoxylated chains) are specifically chosen. Of course, one skilled in the art recognizes that such customization does not only influence water/alcohol solubility and solubilization capability, but may impact other chemical, physical, and mechanical properties.

In various aspects of the invention, the modified natural compound may be soluble in an organic alcohol containing 1-10 carbon atoms. In a particular embodiment, the modified natural oil is soluble in an organic alcohol containing 1-5 carbon atoms. Most particularly, the modified natural compound is soluble in methanol and ethanol. Solubility is measured under standard conditions for temperature and pressure, which are defined above.

When the modified natural oil exhibits solubility in an organic alcohol, then the modified natural compound is at least 1% (w/w) soluble, more particularly is at least 2% (w/w) soluble, and yet inure particularly is at least 5% (w/w) soluble.

In other aspects of the invention, alcohol solubility of the modified natural fatty acid or modified natural oil is not required, such that the solubility descriptions provided in the above paragraphs do not apply.

As an additional benefit, many of the modified natural compounds are believed to be biodegradability. Indeed, many of the starting reactants—fatty acids, triglycerides, and oils—themselves are biodegradable. Without being bound by theory, it is believed that the various modifications described herein may maintain or even enhance biodegradability. This feature may lend the modified, natural compounds to compositions, markets, and uses wherein biodegradability is considered, for example, personal care compositions, coatings, inks, paints, lubricants, products for agriculture, mining and oilfield compositions.

To help the reader understand the full scope of the invention, various and non-limiting examples modified natural oils include:

(a) epoxidized soybean oil reacted with hydroxyethyl pyrrolidone, wherein the epoxide functional groups are partially or fully opened;

(b) epoxidized soybean oil reacted with hydroxyethyl pyrrolidone and methanol, wherein the epoxide functional groups are partially or fully opened;

(c) epoxidized soybean oil reacted with hydroxyethyl pyrrolidone and polyethylene glycol methyl ether, wherein the epoxide functional groups are partially or fully opened; and (d) epoxidized soybean oil reacted with hydroxyethyl pyrrolidone, polyethylene glycol methyl ether, and methanol, wherein the epoxide functional groups are partially or fully opened.

Additional examples of modified natural oils include embraced by the invention include:

maleated soybean oil reacted with hydroxyethyl pyrrolidone, wherein the product may contain unreacted anhydride groups;

maleated soybean oil reacted with hydroxyethyl pyrrolidone and methanol, wherein the product may contain unreacted anhydride groups;

maleated soybean oil reacted with hydroxyethyl pyrrolidone and polyethylene glycol methyl ether, wherein the product may contain unreacted anhydride groups; and maleated soybean oil reacted with hydroxyethyl pyrrolidone, polyethylene glycol methyl ether, and methanol, wherein the product may contain unreacted anhydride groups.

Compositions

In one embodiment, the modified natural fatty acids and modified natural oils are employed in a personal care composition, which encompasses compositions serving the skin, cosmetics, hair (styling and non-styling), and oral care market segments. For example, the personal care compositions having one or more modified natural fatty acids and/or modified natural oils can be used in may used be an oral care composition, a hair care composition, a hair styling composition, a face care composition, a lip care composition, an eye care composition, a foot care composition, a nail care composition, a sun care composition, a deodorant composition, an antiperspirant composition, a cosmetic composition (including color cosmetics), a skin cleaning composition, an insect repellant composition, a shaving composition, a toothpaste, a mouthwash, a tooth whitener, a tooth stain remover, and/or a hygiene composition. Among their many uses, hair care and hair styling compositions find application in enhancing hair shine, cleansing hair, conditioning hair, repairing split ends, enhancing hair manageability, modulating hair stylability, protecting hair from thermal damage, imparting humidity resistance to hair and hair styles, promoting hair style durability, changing the hair color, straightening and/or relaxing hair, and/or providing protection from UV-A and/or UV-B radiation. Other personal care compositions, such as those for skin care and sun care compositions, are useful for protecting from UV-A and/or UV-B radiation, imparting water resistance or water proofness, moisturizing skin, decreasing and/or minimizing the appearance of wrinkles, firming skin, decreasing or minimizing the appearance of skin blemishes (such as lentigo, skin discolorations, pimples, or acne), changing skin color (such as color cosmetics for the face, cheeks, eyelids, or eye lashes). Oral care compositions according to the invention may be used as denture adhesives, toothpastes, mouthwashes, tooth whiteners, and/or stain removers. Personal care compositions also are used for solubilizing, stabilizing, and/or delivering one or more actives (e.g., UV actives, pharmaceutical/nutritional actives, fragrances, flavors, vitamins, minerals, poorly water-soluble materials) to the skin, hair, or oral cavity.

The modified natural compounds described herein may be used alone or in combination with other ingredient(s) in various compositions and product forms. Such compositions include, but are not limited to personal care compositions, adhesives, coatings, paints, electronics, Household, Industrial and Institutional (HI&I) compositions, inks, membranes, metal working fluids, oilfield chemicals, plastics and plasticizers, textiles, industrial products, biocides, pharmaceuticals/nutritionals, and agrochemical compositions.

Non-limiting applications of the hair care compositions include: hair styling, hair setting, hair sculpting, hair curling, hair holding, hair waving, hair fixing, hair maintaining, hair shaping, hair straightening, hair volumizing, hair relaxing, shampooing, hair conditioning, hair cleansing, hair conditioning, promoting hair style durability, imparting humidity resistance to hair and hair styles, enhancing hair shine, repairing split ends of hair, enhancing hair manageability such as lightness, smoothness, softness, disentangling and/or suppleness of hair, modulating hair stylability, protecting hair from thermal damage, hair dyeing, hair coloring, hair bleaching, oxidation dyeing of hair, limiting hair color bleeding, protecting hair color, hair treating (e.g., anti-dandruff), anti-hair fall, and protecting hair from UV radiation.

Non-limiting applications of the sun care compositions include: protecting skin and/or hair from UV radiation (including any or all of UV-A, UV-B and/or UV-C radiation), sun screening, skin anti-irritating, skin repairing, skin wrinkle masking, skin nourishing, skin moisturizing, skin relaxing, skin refreshing, skin cooling, skin soothing, skin tanning, skin tan prolonging, sun-less skin tanning, skin glowing, skin micro-glittering, skin shimmering, and skin anti-tanning.

Non-limiting applications of the skin care compositions include: protecting skin from UV radiation (including any or all of UV-A, UV-B and/or UV-C radiation), skin cleansing, face cleansing, body cleansing, insect repelling, antiperspirant, deodorant, astringent, imparting water resistance or water proofness to skin, decreasing and/or minimizing the appearance of skin wrinkles, decreasing and/or minimizing the appearance of skin blemishes (such as lentigo, skin discolorations, pimples, and/or acne), changing skin color (including skin lightening, skin brightening, skin color darkening, and color cosmetics for the face, cheeks, lips, eyelids, and/or eye lashes), skin iridescing, skin glossing, curling of eye lashes, eye lining, eye shadowing, mascara, removing facial and/or body hair, skin tightening, skin tanning, skin bronzing, skin blushing, prolonging skin tan, sun-less skin tanning, anti-tanning, skin anti-bacterial, skin anti-oxidant, skin anti-photoaging, skin anti-seborrheic, cell exchange and/or cell respiration activating of skin, skin conditioning, skin detoxifying, skin emollient, skin moisturizing, film forming on skin, skin healing-cicatrizing, skin immune-protecting, skin plumping, glossing, shading, plumping, and/or coloring of lips, skin revitalizing, skin energizing, skin re-sculpting, skin nourishing, skin smoothing, skin slimming, skin anti-irritating, and skin sanitizing.

Non-limiting applications of the oral care compositions include: tooth and/or mouth cleansing, providing denture adhesion, delivering and/or retaining actives to oral cavity, mouth washing, mouth refreshing, mouth rinsing, mouth gargling, providing oral hygiene, preventing, reducing, controlling, and/or removing tooth stain, preventing and/or controlling tooth decay, preventing and/or controlling tartar, tooth flossing, tooth whitening and/or bleaching, mouth treating, and tooth filling.

The modified natural compounds described herein also may be used alone or in combination with other ingredient(s) in pharmaceutical and/or nutritional compositions.

Non-limiting applications of the pharmaceutical and/or nutritional compositions include: providing anti-tack, binder, coating, disintegrating, dispersing, encapsulating, filling, film forming, lubricating, and solubilizing. Additional insight into how the modified natural compounds described herein find application in this art area may be found in the following publications by International Specialty Products: *Health and nutrition product guide—Performance enhancing products* (August 2008), *Plasdone® povidones product overview* (April 2010), *Plasdone® K-12 and K-17 providones—Solubilizers for liquid softgel fill formulations* (September 2010), *Plasdone® K-29/32 povidone—High efficiency binder for wet granulation* (April 2010), *Plasdone® S-630 copovidone—Product Overview* (April 2010), *Polyplasdone® Ultra and Ultra-10 crospovidones—Product overview* (September 2010), *Polyplasdone® superdisintegrants—Product overview* (July 2010), *Polyplasdone® crospovidone—Superdisintegrants for orally disintegrating and chewable tablets* (July 2010), *Polyplasdone® crospovidone—Nonionic superdisintegrant for improved dissolution of cationic drugs* (July 2009), *Polyplasdone® crospovidone—The solution for poorly soluble drugs* (July 2009), *Polyplasdone® crospovidone—Novel pelletization aid for extrusion spheronization* (July 2010), *PVP-Iodine povidone iodine antiseptic agent* (March 2004), and *Pharmaceutical technical bulletin—PVP-Iodine for prophylaxis and treatment of bovine mastitis* (December 2003). Each publication is hereby incorporated in its entirety by reference.

The personal care compositions may be formulated in any of the product forms known to a person of ordinary skill in the art. Non-limiting product forms are described below.

Product Forms

Non-limiting hair care product forms include: shampoos, conditioners, aerosols, mousses, sprays, mists, gels, waxes, creams, lotions, glues, pomades, spritzes, solutions, oils, liquids, solids, W/O emulsions, O/W emulsions, suspensions, multiple emulsions, microemulsions, microencapsulated products, sticks, balms, tonics, pastes, reconstitutable products, nanoemulsions, solid lipid nanoparticles, liposomes, cubosomes, neosomes, putties, lacquers, serums, perms, volumizers, packs, flakes, 2-in-1 shampoo/conditioner products, and 3-in-1 shampoo/conditioner/styling products.

Non-limiting sun care product forms include: solutions, liquids, creams, powders, lotions, gels, pastes, waxes, aerosols, sprays, mists, roll-ons, sticks, milks, emulsions, and wipes.

Non-limiting skin care product forms include: solutions, oils, lotions, creams, ointments, liquids, gels, solids, W/O emulsions, O/W emulsions, milks, suspensions, microemulsions, dispersions, microencapsulated products, sticks, balms, tonics, pastes, mists, reconstitutable products, peels, soaps, aerosols, mousses, waxes, glues, pomades, spritzes, putties, lacquers, serums, perms, powders, pencils, flakes, blush, highlighters, bronzers, concealers, and 2-way cake products.

The six skin care product categories that follow next may be considered a subset of the skin and sun care products:

(1) Eye Care

Non-limiting eye care product forms include: mascaras, eye liners, eye shadows, curlers of eye lashes, eyebrow pencils, and eye pencils.

(2) Lip Care

Non-limiting lip care product forms include: lipsticks, lip balms, lip pencils, lip glosses, lip sprays, transparent lip bases, tinted lip moisturizers, and multi-functional color sticks that can also be used for cheeks and eyes.

(3) Nail Care

Non-limiting nail care product forms include: nail polishes, nail varnishes, enamels, nail varnish removers, home-manicure products such as cuticle softeners and nail strengtheners, and artificial nails.

(4) Face Care

Non-limiting face care product forms include: creams, lotions, solutions, oils, liquids, peels, scrubs, emulsions, suspensions, microemulsions, microencapsulated product, pastes, reconstitutable product, aerosols, mousses, gels, waxes, glues, pomades, spritzes, facial wet-wipes, putties, lacquers, serums, perms, powders, blush, highlighters, bronzers, masks, and concealers.

(5) Body Care

Non-limiting body care product forms include: foams, peels, masks, gels, sticks, aerosols, lotions, salts, oils, balls, liquids, powders, peels, pearls, bar soaps, liquid soaps, body washes, cleansers, scrubs, creams, flakes, other bath and shower products, shaving products, waxing products, and sanitizers.

(6) Foot Care

Non-limiting foot care product forms include: mousses, creams, lotions, powders, liquids, sprays, aerosols, gels, flakes, and scrubs.

Non-limiting oral care product forms include: toothpastes, adhesives, gums, gels, powders, creams, solutions, lotions, liquids, dispersions, suspensions, emulsions, tablets, capsules, rinses, flosses, aerosols, strips, films, pads, bandages, microencapsulated products, syrups, and lozenges.

Also contemplated are personal care compositions comprising polymer(s) described herein complexed with iodine. These compositions may be used in treating skin conditions, non-limiting examples of which include dermatitis, wounds, bacterial infections, burns, rashes, and herpes. These complexed compositions may be staining, substantially non-staining, or essentially non-staining.

Examples of related personal care compositions are disclosed in U.S. Pat. Nos. 5,599,800; 5,650,166; 5,916,549; and 6,812,192; U.S. patent application 2009/0317432; EP 556,660; 661,037; 661,038; 662,315; 676,194; 796,077;

970,682; 976383; 1,415,654; and 2,067,467; and WO 2005/032506; each of which is hereby incorporated in its entirety by reference.

It is also contemplated that the personal care compositions may be used in products for male and/or female personal grooming and/or toiletry such as; sanitary napkins, baby diapers, adult diapers, feminine products, products for incontinence, and other related products.

An array of additional personal care compositions, methods, and uses are contemplated. Disclosure of these compositions may be found in the following brochures by International Specialty Products, each of which is hereby incorporated in its entirety by reference: *Plasdone® K-29/32*, *Advanced non-oxidative, non-abrasive teeth whitening in toothpasts, mouthwashes, and oral rinses* (2010), *Polymers for oral care, product and applications guide* (2002), *A formulation guide for excellent hair styling gels and lotions* (April 2003), *PVP (polyvinylpyrrolidone)* (no date provided), and *Textile chemicals, solutions for the most challenging product environment* (no date provided).

Also contemplated are additional personal care compositions that may comprise the modified natural compounds described herein. Disclosures on such compositions may be found in the publications listed below, each of which is hereby incorporated in its entirety be reference: (1) *Prototype Formulations—Personal Care Products* (2009) from Xiameter, Dow Corning. (2) *Sun care formulations tinder the category "Refreshing Sun", "Younger Sun", "Sun for Men", and "Sunny Glow"* from Dow Corning. (3) *Cosmetic Nanotechnology, Polymers and Colloids in Cosmetics*, 2007, ACS Symposium Series. (4) Review Paper: "Lipid nanoparticles" (SLN, NLC) in cosmetic and pharmaceutical dermal products, International Journal of Pharmaceutics, Volume 366, 2009.

Optional: Additional Composition Ingredients

It is also contemplated that the personal care compositions optionally may contain one or more additional ingredients.

Further, it is contemplated that the composition ingredients may be formulated in a single container, or the ingredients may be formulated in-part in two or more distinct containers of the same or different type, the contents of which may require mixing prior to use.

Furthermore, it also is contemplated that the compositions may be prepared in the form of concentrates that may be diluted by a suitable substance(s) prior to use. The concentrate may, in turn, be present in any of the forms as described under 'Product Forms' for the personal care compositions of the invention.

A non-limiting list of classes of additional ingredients that may optionally be present in different types of personal care compositions is provided below: conditioning agents, antimicrobials, protectives (for example, antiradical agents), abrasives, UV absorbers, emulsifiers (including, but not limited to ethoxylated fatty acids, ethoxylated glyceryl esters, ethoxylated oils, ethoxylated sorbitan esters, fatty esters, PEG esters, polylycerol esters), antiperspirants (including, but not limited to aluminium chlorohydrates, aluminium zirconium chlorhydrates), antioxidants, vitamins and/or provitamins, botanicals, fixatives, oxidizing agents, reducing agents, dyes, cleansing agents, anionic, cationic, nonionic, and/or amphoteric surfactants, thickeners and/or gelling agents, perfumes, flavors, and/or fragrances, pearlizing agents, stabilizers, pH adjusters, filters, antimicrobial agents, preservatives and/or disinfectants, associative polymers, oils of vegetable, mineral, and/or synthetic origin, polyols, silicones, colorants, bleaching agents, highlighting agents, propellants (including, but not limited to hydrocarbons, dimethyl ether, fluorocarbons), styling polymers, benefit agents, skin lighteners (including, but not limited to arbutin and kojic acids), tanning agents (including, but not limited to dihydroxyacetone), solvents and/or cosolvents, diluents, essential oils, sequestrants and/or chelators, carriers, and natural extracts and/or natural products.

The amount of each ingredient in the composition varies depending on the type of composition, the function and/or physicochemical property of the ingredient, and the amount of other co-ingredients. The precise amount of each ingredient may be easily determined by any person skilled in the related arts.

It may be desirable to include one or more ingredients described in the prior art disclosures IPCOM000186541D, IPCOM000128968D, and IPCOM000109682D on www.ip.com, the contents of each of these disclosures are hereby incorporated in their entirety by reference.

Further reference to formulary co-ingredients and product forms include the disclosures in US 2010/0183532, paragraphs [0096]-[0162], and WO 2010/105050, paragraphs [0053]-[0069], the contents of which are hereby incorporated in their entirety by reference, Any known conditioning agent may be used in the personal care compositions of the invention. An extensive discussion on conditioining agents may be found in the book *Conditioning Agents for Skin and Hair, Cosmetic Science and Technology Series*, Volume 21, 1999, Marcel Dekker Publishers. The contents of the book is hereby incorporated in its entirety by reference.

Conditioning agents may be chosen from synthetic oils, mineral oils, vegetable oils, fluorinated or perfluorinated oils, natural or synthetic waxes, silicones, cationic polymers, proteins and hydrolyzed proteins, cationic surfactants, ceramide type compounds, fatty amines, fatty acids and their derivatives, as well as mixtures of these different types of compounds.

Non-limiting examples of suitable synthetic oils include: polyolefins, e.g., poly-α-olefins, such as polybutenes, polyisobutenes, polydecenes, and blends thereof. The polyolefins may be hydrogenated.

Non-limiting examples of suitable mineral oils include hexadecane and oil of paraffin.

Non-limiting examples of suitable animal and vegetable oils include: sunflower oil, corn oil, soy oil, avocado oil, jojoba oil, squash oil, raisin seed oil, sesame seed oil, walnut oil, fish oil, glycerol tricaprocaprylate, purcellin oil, liquid jojoba, and blends thereof. Also suitable are natural oils such as oils of eucalyptus, lavender, vetiver, litsea cubeba, lemon, sandalwood, rosemary, chamomile, savory, nutmeg, cinnamon, hyssop, caraway, orange, geranium, cade, bergamot, and blends thereof.

The conditioning agent may be a fluorinated or a perfluorinated oil. The fluoridated oils may also be fluorocarbons such as fluoramines, e.g., perfluorotributylamine, fluoridated hydrocarbons such as perfluorodecahydronaphthalene, fluoroesters, fluoroethers, and blends thereof.

Non-limiting examples of suitable natural and synthetic waxes include: carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax, and blends thereof.

The conditioning agent may be any silicone known by those skilled in the art. Silicones include polyorganosiloxanes that are insoluble in the composition. The silicones may be present in the form of oils, waxes, resins, or gums. They may be volatile or non-volatile.

Non-limiting examples of suitable silicones include: polyalkyl siloxanes, polyaryl siloxanes, polyalkyl aryl siloxanes, silicone gums and resins, polyorgano siloxanes modified by organofunctional groups, and blends thereof.

Suitable polyalkyl siloxanes include polydimethyl siloxanes with terminal trimethyl silyl groups or terminal dimethyl silanol groups (dimethiconol) and polyalkyl (C1-C20) siloxanes. Suitable polyalkyl aryl siloxanes include polydimethyl methyl phenyl siloxanes and polydimethyl diphenyl siloxanes. The siloxanes can have a linear or branched structure.

Suitable silicone gums include polydiorganosiloxanes, such as those having a number-average molecular weight between 200,000 Da and 1,000,000 Da used alone or mixed with a solvent.

Non-limiting examples of suitable silicone gums include: polymethyl siloxane, polydimethyl siloxane/methyl vinyl siloxane gums, polydimethyl siloxane/diphenyl siloxane, polydimethyl siloxane/phenyl methyl siloxane, polydimethyl siloxane/diphenyl siloxane/methyl vinyl siloxane, and blends thereof.

Non-limiting examples of suitable silicone resins include silicones with a dimethyl/trimethyl siloxane structure and resins of the trimethyl siloxysilicate type.

The organo-modified silicones suitable for use in the invention include silicones such as those previously defined and containing one or more organofunctional groups attached by means of a hydrocarbon radical, and grafted silicone polymers. The organo-modified silicones may be one from the amino functional silicone family.

The silicones may be used in the form of emulsions, nano-emulsions, or micro-emulsions.

The cationic polymers that may be used as conditioning agents according to the invention generally have a molecular weight (average number) from about 500 Da to about 5,000,000 Da, and particularly from about 1,000 Da to about 3,000,000 Da. The expression "cationic polymer" as used herein indicates any polymer having at least one cationic group.

The cationic polymers may be chosen from among polymers containing primary, secondary, tertiary amine, and/or quaternary ammonium groups that may form part of the main polymer backbone and/or side chain(s).

Non-limiting examples of suitable cationic polymers include polyamines, polyaminoamides, and quaternary polyammonium classes of polymers, such as:

(1) homopolymers and copolymers derived from acrylic or methacrylic esters or amides. The copolymers may contain one or more units derived from acrylamides, methacrylamides, diacetone acrylamides, acrylic or methacrylic acids or their esters, vinyllactams such as vinyl pyrrolidone or vinyl caprolactam, and vinyl esters. Non-limiting, specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone and dialkylaminoalkyl acrylate or methacrylate, optionally quaternized, such as the products sold under the name Gafquat® by International Specialty Products; terpolymers of dimethyl amino ethyl methacrylate, vinyl caprolactam, and vinyl pyrrolidone such as the product sold under the name Gaffix® VC 713 by International Specialty Products; the vinyl pyrrolidone/methacrylamidopropyl dimethylamine copolymer, marketed under the name Styleze® CC 10 by International Specialty Products; and the vinyl pyrrolidone/quaternized dimethyl amino propyl methacrylamide copolymers such as the product sold under the name Gafquat® HS 100 by International Specialty Products (Wayne, N.J.).

(2) derivatives of cellulose ethers containing quaternary ammonium groups, such as hydroxy ethyl cellulose quaternary ammonium that has reacted with an epoxide substituted by a trimethyl ammonium group.

(3) derivatives of cationic cellulose such as cellulose copolymers or derivatives of cellulose grafted with a hydrosoluble quaternary ammonium monomer, as described in U.S. Pat. No. 4,131,576, such as hydroxy alkyl cellulose, and hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.

(4) cationic polysaccharides such as described in U.S. Pat. Nos. 3,589,578 and 4,031,307, guar gums containing cationic trialkyl ammonium groups, and guar gums modified by a salt, e.g., chloride of 2,3-epoxy propyl trimethyl ammonium.

(5) polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.

(6) water-soluble polyamino amides prepared by polycondensation of an acid compound with a polyamine. These polyamino amides may be reticulated.

(7) derivatives of polyamino amides resulting from the condensation of polyalkylene polyamines with polycarboxylic acids followed by alkylation by bi-functional agents.

(8) polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers include those described in U.S. Pat. Nos. 3,227,615 and 2,961,347.

(9) cyclopolymers of alkyl diallyl amine or dialkyl diallyl ammonium such as the homopolymer of dimethyl diallyl ammonium chloride and copolymers of diallyl dimethyl ammonium chloride and acrylamide.

(10) quaternary diammonium polymers such as hexadimethrine chloride.

(11) quaternary polyammonium polymers, including, for example, Mirapol® A 15, Mirapol® AD1, Mirapol® AZ1, and Mirapol® 175 products sold by Miranol.

(12) quaternary polymers of vinyl pyrrolidone and vinyl imidazole such as the products sold under the names Luviquat® FC 905, FC 550, and FC 370 by BASF Corporation.

(13) quaternary polyamines.

(14) reticulated polymers known in the art.

Other cationic polymers that may be used include cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin.

The conditioning agent may comprise a protein or hydrolyzed cationic or non-cationic protein. Non-limiting examples of suitable compounds include: hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one C1-C18 alkyl, and blends thereof.

Non-limiting examples of suitable hydrolyzed cationic proteins include: Croquat® L, in which the quaternary ammonium groups include a C12 alkyl group, Croquat® M, in which the quaternary ammonium groups include C10-C18 alkyl groups, Croquat® S in which the quaternary ammonium groups include a C18 alkyl group, Crotein® Q in which the quaternary ammonium groups include at least one C1-C18 alkyl group, and blends thereof. These products are sold by Croda.

The conditioning agent may also comprise quaternized vegetable protein(s) such as wheat, corn, or soy proteins, non-limiting examples of which include: cocodimonium hydrolyzed wheat protein, laurdimonium hydrolyzed wheat protein, steardimonium hydrolyzed wheat protein, 2-N-stearoyl amino-octadecane-1,3-diol, 2-N-behenoyl amino-oetadecane-1,3-diol, 2-N-[2-hydroxy-palmitoyl]-amino-octadecane-1,3-diol, 2-N-stearoyl amino-octadecane-1,3,4-triol, N-stearoyl phytosphingosine, 2-N-palmitoyl amino-hexadecane-1,3-diol, bis-(N-hydroxy ethyl N-cetyl) malonamide, N-(2-hydroxy ethyl)-N-(3-cetoxyl-2-hydroxy propyl) amide of cetylic acid, N-docosanoyl N-methyl-D-glucamine, and blends thereof.

The conditioning agent may also comprise a cationic surfactant such as a salt of a primary, secondary, or tertiary fatty amine, optionally polyoxyalkylenated, a quaternary ammonium salt, a derivative of imadazoline, or an amine oxide. Conditioning agents may also be selected from the group consisting of: mono-, di-, and tri-alkyl amines, and quaternary ammonium compounds with a counterion such as a chloride, a methosulfate, a tosylate, etc. Non-limiting examples of suitable amines include: cetrimonium chloride, dicetyldimonium chloride, behentrimonium methosulfate, and blends thereof.

The conditioning agent may comprise a fatty amine. Non-limiting examples of suitable fatty amines include: dodecyl amines, cetyl amines, stearyl amines such as stearamidopropyl dimethylamine, and blends thereof.

The conditioning agent may comprise a fatty acid or derivative(s) thereof. Non-limiting examples of suitable fatty acids include: myristic acid, palmitic acid, stearic acid, behenic acid, oleic acid, linoleic acid, isostearic acid, and blends thereof. The derivatives of fatty acids include carboxylic ester acids including mono-, di-, tri- and tetra-carboxylic acids esters, amides, anhydrides, esteramides, imides, and mixtures of these functional groups.

Also suitable as conditioning agents are the following commercial products:

(1) Aquacat™ Clear Cationic Solution (INCI Name: guar hydroxypropyltrimonium Chloride), N-Hance™ SP-100 (INCI Name: acrylamidopropyl trimonium chloride/acrylamide copolymer), and N-Hance™ cationic guar (INCI Name: guar hydroxypropyltrimonium chloride) from Ashland Inc.

(2) Salcare® from BASF Corp.

(3) Sotcat™ Polymers from The Dow Chemical Company.

(4) Jaguar® C500, Polycare® Boost, Mackconditioner™ Brite, and Mackine® 301 from Rhodia.

(5) Stepanquat® ML, Stepanquat® GA-90, Ninol®, and Ammonyx® from Stepan Company.

Of course, mixtures of two or more conditioning agents may be used.

The conditioning agent(s) may be present in an amount from about 0.001% to about 20%, particularly from about 0.01% to about 10%, and even more particularly from about 0.1% to about 3% by weight of the composition.

Personal care compositions may optionally comprise antimicrobial agent(s).

Non-limiting examples of suitable water insoluble, non-cationic antimicrobial agents include: halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, halogenated carbanilides, and blends thereof.

Non-limiting examples of suitable water soluble antimicrobial agents include: quaternary ammonium salts, bisbiquanide salts, triclosan monophosphate, and blends thereof.

The quaternary ammonium agents include those in which one or two of the substituents on the quaternary nitrogen has a carbon chain length (typically alkyl group) from about 8 to about 20, typically from about 10 to about 18 carbon atoms, while the remaining substituents (typically alkyl or benzyl group) have a lower number of carbon atoms, such as from about 1 to about 7 carbon atoms, typically methyl or ethyl groups.

Non-limiting examples of suitable quaternary ammonium antibacterial agents include: Dodecyl trimethyl ammonium bromide, tetradecylpyridinium chloride, domiphen bromide, N-tetradecyl-4-ethyl pyridinium chloride, dodecyl dimethyl (2-phenoxyethyl)ammonium bromide, benzyl dimethyl-stearyl ammonium chloride, cetyl pyridinium chloride, quaternized 5-amino-1,3-bis(2-ethyl-hexyl)-5-methyl hexahydropyrimidine, benzalkonium chloride, benzethonium chloride, methyl benzethonium chloride, and blends thereof.

Other antimicrobial compounds are bis[4-(R-amino)-1-pyridinium]alkanes as disclosed in U.S. Pat. No. 4,206,215. Other antimicrobials such as copper salts, zinc salts and/or stannous salts may also be included. Also useful are enzymes, including endoglycosidase, papain, dextranase, mutanase, and blends thereof. Such antimicrobial agents are disclosed in U.S. Pat. Nos. 2,946,725 and 4,051,234. The antimicrobial agents may also comprise chlorhexidine, triclosan, and flavor oils such as thymol. Triclosan and other agents are disclosed in U.S. Pat. Nos. 5,015,466 and 4,894,220.

In some embodiments, it may be preferable to incorporate one or more preservatives.

Non-limiting examples of suitable preservatives include: benzoic acid, sorbic acid, dehydroacetic acid, diazolidinyl ureas, imidazolidinyl ureas, salicylic acid, piroctone olamine, DMDM hydantoin, IPBC (iodopropynyl butylcarbamate), triclosan, bronopol, formaldehyde, isothiazolinones, nitrates/nitrites, parabens, phenoxyethanol, potassium sorbate, sodium benzoate, sulphites, sulphur dioxide, and blends thereof.

In some embodiments, it may be preferable to incorporate preservative boosters/solvents, non-limiting examples of which include: caprylyl glycol, hexylene glycol, pentylene glycol, ethylhexylglycerin, caprylhydroxamic acid, caprylohydroxamic acid, glyceryl caprylate, and blends thereof.

Polysaccharides, such as gum Arabic, may be included as well.

Personal care compositions may comprise liquid or liquid-like carrier(s) that help to distribute, disperse, and/or dissolve the ingredients.

Non-limiting examples of suitable liquid carriers include: water, alcohols, oils, esters, and blends thereof.

Typically, sun care compositions may also comprise one or more UV actives, which include organic and inorganic materials that scatter, absorb, and/or reflect radiation having a wavelength from about 100 nm to about 400 nm.

In one particular embodiment, the sun care compositions protect against UV-A, UV-B, and/or UV-C radiation.

UV-A radiation, from about 320 nm to about 400 nm, has the longest wavelengths within the UV spectrum, and consequently is the least energetic. UV-A radiation includes UV-A1 (from about 340 nm to about 400 nm) and UV-A2 (from about 320 nm to about 340 nm). UV-B radiation has shorter wavelengths, from about 290 nm to about 320 nm. UV-C radiation has the shortest wavelengths from about 200 nm to about 290 nm.

In another embodiment, the sun care compositions may not contain UV actives, and may be regarded as tanning oils or tan promoters.

Sun care compositions may be formulated, for example, for application to the lips, hair, cheeks, neck or the area around the eyes. Self-tanning compositions, which are products that color skin without requiring full sun exposure, also fit under the sun care umbrella.

Suitable UV absorber(s) that may be included in the personal care compositions most likely will depend on local regulations. As the rules governing the names and usage levels evolve over time, it is impossible to include every UV absorber that may be used with the invention.

Non-limiting examples of suitable UV absorbers include: octyl salicylate; pentyl dimethyl PABA; octyl dimethyl PABA; benzophenone-1; benzophenone-6; 2-(2H-benzotriazole-2-yl)-4,6-di-tert-pentylphenol; ethyl-2-cyano-3,3-diphenylacrylate; homomethyl salicylate; bis-ethylhexyloxyphenol methoxyphenyl triazine; methyl-(1,2,2,6,6-pentamethyl-4-piperidyl)-sebacate; 2-(2H-benzotriazole-2-yl)-4-methylphenol; diethylhexyl butamido triazone; amyl dimethyl PABA; 4,6-bis(octylthiomethyl)-o-cresol; CAS number 65447-77-0; red petroleum; ethylhexyl triazone; octocrylene; isoamyl-p-methoxycinnamate; drometrizole; titanium dioxide; 2,4-di-tert-butyl-6-(5-chloro-2H-benzotriazole-2-yl)-phenol; 2-hydroxy-4-octyloxybenzophenone; benzophenone-2; diisopropyl methylcinnamate; PEG-25 PABA; dimethylethyl)-6-[[3-(1,1-demethylethyl)-2-hydroxy-5-methylphenyl]methyl-4-methylphenyl acrylate; drometrizole trisiloxane; menthyl anthranilate; butyl methoxydibenzoylmethane; 2-ethoxyethyl p-methoxycinnamate; benzylidene camphor sulfonic acid; dimethoxyphenyl-[1-(3,4)]-4,4-dimethyl 1,3-pentanedione; zinc oxide; N,N'-hexane-1,6-diylbis[3-(3,5-di-tert-butyl-4-hydroxyphenylpropionamide)]; pentaerythritol tetrakis[3-(3,5-di-tert-butyl-4-hydroxyphenyl)propionate]; 2,6-di-tert-butyl-4-[4,6-bis(octylthio)-1,3,5-triazin-2-ylamino]phenol; 2-(2H-benzotriazole-2-yl)-4,6-bis(1-methyl-1-phenylethyl)phenol; trolamine salicylate; diethylanolamine p-methoxycinnamate; polysilicone-15; CAS number 152261-33-1; 4-methylbenzylidene camphor; bisoctrizole; N-phenyl-benzenamine; reaction products with 2,4,4-trimethylpentene; sulisobenzone; (2-ethylhexyl)-2-cyano-3,3-diphenylacrylate; digalloyl trioleate; polyacrylamido methylbenzylidene camphor; glyceryl ethylhexanoate dimethoxycinnamate; 1,3-bis-[(2'-cyano-3',3'-diphenylacryloyl)oxy]-2,2-bis-{[(2'-cyano-bis-(2,2,6,6-tetramethyl-4-piperidyl)-sebacate; benzophenone-5; 1,3,5-tris(3,5-di-tert-butyl-4-hydroxybenzyl)-1,3,5-triazine-2,4,6(1H,3H,5H)-trione; hexamethylendiamine; benzophenone-8; ethyl-4-bis(hydroxypropyl) aminobenzoate; 6-tert-butyl-2-(5-chloro-2H-benzotriazole-2-yl)-4-methylphenol; p-aminobenzoic acid; 3,3',3'',5,5',5''-hexa-tert-butyl-α-α'-α''-(mesitylene-2,4,6-triyl)tri-p-cresol; lawsone with dihydroxyacetone; benzophenone-9; benzophenone-4; ethylhexyl dimethoxy benzylidene dioxoimidazoline propionate; N,N'-bisformyl-N,N'-bis-(2,2,6,6-tetramethyl-4-piperidinyl)-; 3-benzylidene camphor; terephthalylidene dicamphor sulfonic acid; camphor benzalkoniutn methosulfate; bisdisulizole disodium; etocrylene; ferulic acid; 2-(2H-benzotriazole-2-yl)-4-(1,1,3,3-tetramethylbutyl)-phenol; 4,6-bis(dodecylthiomethyl)-o-cresol; β-2-glucopyranoxy propyl hydroxy benzophenone; phenylbenzimidazole sulfonic acid; benzophenone-3; diethylamine hydroxybenzoyl hexylbenzoate; 3',3'-diphenylacryloyl)oxy]methyl}-propane; ethylhexyl p-methoxycinnamate, and blends thereof.

Personal care compositions may comprise antioxidant(s) and/or antiradical protecting agent(s).

Non-limiting examples of suitable antioxidants and/or antiradical protecting agents include: BHA (tert-butyl-4-hydroxy anisole), BHT (2,6-di-tert-butyl-p-cresol), TBHQ butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, lactoferrin, and blends thereof.

Personal care compositions may comprise vitamin(s), provitamin(s), and/or mineral(s).

Non-limiting examples of suitable vitamins include: ascorbic acid (vitamin C), vitamin E, vitamin E acetate, vitamin E phosphate, B vitamins such as B3 and B5, niacin, vitamin A, derivatives thereof, and blends thereof.

Non-limiting examples of suitable provitamins include: panthenol, retinol, and blends thereof.

Non-limiting examples of suitable minerals include: talc, clay, calcium carbonate, silica, kaolin, mica, and blends thereof. Further examples of minerals that may be used in the personal care compositions may be found in a brochure titled Minerals for Personal Care from Imerys Performance Minerals, the disclosure of which is hereby incorporated in its entirety by reference.

Personal care compositions may comprise one or more surfactants. Surfactants serve in solubilizing, dispersing, emulsifying and/or reducing the interfacial tension. Surfactants may be chosen from anionic, nonionic, amphoteric, zwitterionic, or cationic surfactants, or blends thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are non-limiting examples of anionic surfactants of this type.

Non-limiting examples of suitable anionic surfactants include: sarcosinates, taurates, isethionates, sodium lauryl sulfoacetate, sodium laureth carboxylate, and sodium dodecyl benzenesulfonate. Also suitable are alkali metal or ammonium salts of surfactants such as the sodium and potassium salts of the following: lauroyl sarcosinate, myristoyl sarcosinate, palmitoyl sarcosinate, stearoyl sarcosinate, and oleoyl sarcosinate.

Non-limiting examples of suitable cationic surfactants include: derivatives of aliphatic quaternary ammonium compounds having at least one long alkyl chain containing from about 8 to about 18 carbon atoms, such as, lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, cetyl pyridinium fluoride, and blends thereof. Further suitable are quaternary ammonium fluorides having detergent properties such as compounds described in U.S. Pat. No. 3,535,421. Certain cationic surfactants may act as germicides in the compositions disclosed herein.

Nonionic surfactants useful herein include compounds produced by the condensation of alkylene oxide groups (hydrophilic in nature) with an organic hydrophobic compound which may be aliphatic or alkylaromatic in nature.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Other surfactants such as fluorinated surfactants may also be incorporated within the compositions of the invention.

Also suitable as surfactants are the following commercial products:

(1) Alkanolamides, under the trade names Amidex™ and Schercomid™; amido-amines, under the trade names Katemul™ and Schercodine™; amine oxides, under the trade names Chemoxide™ and Schercamox™; amphoterics, under the trade names Chembetaine™, Schercotaine™ and Schercoteric™; imidazolines, under the trade name Schercozoline™; pearlizing agents, under the trade name Quickpearl™; performance concentrates, under the trade names Sulfochem™ and Chemoryl™; soaps (potassium cocoate and potassium soyate); specialty ethoxylates, under the trade name Chemonic™; specialty quats under the trade names Quatrex™ and Schercoquat™; sulfates, under the trade name Sulfochem™; and sulfosuccinates, under the trade name Chemccinate™ from Lubrizol.

(2) Avaniel, Cremaphore®, Jordapan®, and Pluracare® from BASF Corp.

(3) Miracare® SLB, Mackam® Bab, Mackanate® Ultra SI, Miranol® Ultra, and Miracare® Plaisant from Rhodia.

(4) Stepan® Pearl 2, Stepan® Pearl 4, Stepan® Pearl Series, Neobee® M-20, Stepan® PTC, Amphosol® 2CSF, Steol®, Stepan-Mild® GCC, Stepan® SLL-FB, Stepanol® AM, Stepanol® PB, Alpha-Step® BSS-45, Bio-Terge® 804, Stepan-Mild® L3, Stepan® SLL-FB, Stepan® SSL-CG, and Stepanol® CFAS-70 from Stepan Company.

Also suitable as surfactants are those described in the book Surfactants in Personal Care Products and Decorative Cosmetics, Third Edition, 2006, CRC Press, The disclosure is incorporated hereby in its entirety by reference.

Personal care compositions may be also be formulated as detergent compositions, such as shampoos, bath gels, and bubble baths. Such compositions comprise water as a liquid carrier. The surfactant or surfactants that form the washing base may be chosen alone or in blends, from known anionic, amphoteric, zwitterionic and/or non-ionic surfactants. The quantity and quality of the washing base must be sufficient to impart a satisfactory foaming and/or detergent value to the final composition. The washing base may be present in an amount from about 4% to about 50% by weight, particularly from about 6% to about 35% by weight, and more particularly from about 8% to about 25% by weight of the final composition.

Personal care compositions may comprise one or more thickener(s) and/or viscosifier(s).

Non-limiting examples of suitable thickeners and/or viscosifiers include: Acetamide MEA; acrylamide/ethalkonium chloride acrylate copolymer; acrylamide/ethyltrimonium chloride acrylate/ethalkonium chloride acrylate copolymer; acrylamides copolymer; acrylamide/sodium acrylate copolymer; acrylamide/sodium acryloyldimethyltaurate copolymer; acrylates/acetoacetoxyethyl methacrylate copolymer; acrylates/beheneth-25 methacrylate copolymer; acrylates/C10-C30 alkyl acrylate crosspolymer; acrylates/ceteth-20 itaconate copolymer; acrylates/ceteth-20 methacrylate copolymer; acrylates/laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer; acrylates/steareth-20 methacrylate copolymer; acrylates/stearyl methacrylate copolymer; acrylates/vinyl isodecanoate crosspolymer; acrylic acid/acrylonitrogens copolymer; adipic acid/methyl DEA crosspolymer; agar; agarose; alcaligenes polysaccharides; algin; alginic acid; almondamide DEA; almondamidopropyl betaine; aluminum/magnesium hydroxide stearate; ammonium acrylates/acrylonitrogens copolymer; ammonium acrylates copolymer; ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; *arachis hypogaea* (peanut) flour; ascorbyl methylsilanol pectinate; astragalus gummifer gum; attapulgite; *avena sativa* (oat) kernel flour; avocadamide DEA; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; caesalpinia spinosa gum; calcium alginate; calcium carboxymethyl cellulose; calcium carrageenan; calcium chloride; calcium potassium carbomer; calcium starch octenylsuccinate; C20-40 alkyl stearate; canolamidopropyl betaine; capramide DEA; capryl/capramidopropyl betaine; carbomer; carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar; carnitine; cellulose acetate propionate carboxylate; cellulose gum; ceratonia siliqua gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; *citrus aurantium dulcis* (orange) peel extract; cocamide DEA; cocamide MEA; cocamide MIPA; cocamidoethyl betaine; cocamidopropyl betaine; cocamidopropyl hydroxysultaine; cocobetaine; coco-hydroxysultaine; coconut alcohol; coco/oleamidopropyl betaine; coco-Sultaine; cocoyl sarcosinamide DEA; cornamide/cocamide DEA; cornamide DEA; croscarmellose; crosslinked bacillus/glucose/sodium glutamate ferment; *cyamopsis tetragonoloba* (guar) gum; decyl alcohol; decyl betaine; dehydroxanthan gum; dextrin; dibenzylidene sorbitol; diethanolaminooleamide DEA; diglycol/CHDM/isophthalates/SIP copolymer; dihydroabietyl behenate; dihydrogenated tallow benzylmonium hectorite; dihydroxyaluminum aminoacetate; dimethicone/PEG-10 crosspolymer; dimethicone/PEG-15 crosspolymer; dimethicone propyl PG-betaine; dimethylacrylamide/acrylic acid/polystyrene ethyl methacrylate copolymer; dimethylacrylamide/sodium acryloyldimethyltaurate crosspolymer; disteareth-100 IPDI; DMAPA acrylates/acrylic acid/acrylonitrogens copolymer; erucamidopropyl hydroxysultaine; ethylene/sodium acrylate copolymer; gelatin; gellan gum; glyceryl alginate; *glycine soja* (soybean) flour; guar hydroxypropyltrimonium chloride; hectorite; hyaluronic acid; hydrated silica; hydrogenated potato starch; hydrogenated tallow; hydrogenated tallowamide DEA; hydrogenated tallow betaine; hydroxybutyl methylcellulose; hydroxyethyl acrylate/sodium acryloyldimethyl taurate copolymer; hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylenediamine carbomer; hydroxypropyl guar; hydroxypropyl methylcellulose; hydroxypropyl methylcellulose stearoxy ether; hydroxypropyl starch; hydroxypropyl starch phosphate; hydroxypropyl xanthan gum; hydroxystearamide MEA; isobutylene/sodium maleate copolymer; isostearamide DEA; isostearamide MEA; isostearamide mIPA; isostearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether; lauryl sultaine; lecithinamide DEA; linoleamide DEA; linoleamide MEA; linoleamide MIPA; lithium magnesium silicate; lithium magnesium sodium silicate; *macrocystis pyrifera* (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; milkamidopropyl betaine; minkamide DEA; minkamidopropyl betaine; MIPA-myristate; montmorillonite; Moroccan lava clay; myristamide DEA; myristamide MEA; myristamide MIPA; myristamidopropyl betaine; myristamidopropyl hydroxysultaine; myristyl alcohol; myristyl betaine; natto gum; nonoxynyl hydroxyethylcellulose; oatamide MEA; oatamidopropyl betaine; octacosanyl glycol isostearate; octadecene/MA copolymer; oleamide DEA; oleamide MEA; oleamide MIPA; oleamidopropyl betaine; oleamidopropyl hydroxysultaine; oleyl betaine; olivamide DEA; olivamidopropyl betaine; oliveamide MEA; palmamide DEA; palmamide MEA; palmamide MIPA; palmamidopropyl betaine; palmitamide DEA; palmitamide MEA; palmitamidopropyl betaine; palm kernel alcohol; palm kernelamide DEA; palm kernelamide MEA; palm kernelamide MIPA; palm kernelamidopropyl betaine; peanutamide MEA; peanutamide MIPA; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/laureth-50/™MG copolymer; PEG-10/lauryl dimethicone crosspolymer; PEG-15/lauryl dimethicone crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/™MG copolymer; PEG-150 pentaerythrityl tetrastearate; PEG-4 rapeseedamide; PEG-150/stearyl alcohol/SMDI copolymer; phaseolus angularis seed powder; polianthes tuberosa extract; polyacrylate-3; polyacrylic acid; polycyclopentadiene; polyether-1; polyethylene/isopropyl maleate/MA copolyol; polyglyceryl-3 disiloxane dimethicone; polyglyceryl-3 polydimethylsiloxyethyl dimethicone; polymethacrylic acid; polyquaternium-52; polyvinyl alcohol; potassium alginate; potassium aluminum polyacrylate; potassium carbomer; potassium carrageenan; potassium chloride; potassium palmate; potassium polyacrylate; potassium sulfate; potato starch modified; PPG-2 cocamide; PPG-1 hydroxyethyl caprylamide; PPG-2 hydroxyethyl cocamide; PPG-2 hydroxyethyl coco/isostearamide; PPG-3 hydroxyethyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; *pyrus cydonia* seed; *pyrus malus* (apple) fiber; rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; rosa multiflora flower wax; sclerotium gum; sesamide DEA; sesamidopropyl betaine; sodium acrylate/acryloyldimethyl taurate copolymer; sodium acrylates/acrolein copolymer; sodium acrylates/acrylonitrogens copolymer; sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer; sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate; sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acid/acrylonitrogens copolymer; sodium tocopheryl phosphate; *solanum tuberosum* (potato) starch; soyamide DEA; soyamidopropyl betaine; starch/acrylates/acrylamide copolymer; starch hydroxypropyltrimonium chloride; stearamide AMP; stearamide DEA; stearamide DEA-distearate; stearamide DIBA-stearate; stearamide MEA; stearamide MEA-stearate; stearamide MIPA; stearamidopropyl betaine; steareth-60 cetyl ether; steareth-100/PEG-136/HDI copolymer; stearyl alcohol; stearyl betaine; sterculia urens gum; synthetic fluorphlogopite; tallamide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; tamarindus indica seed gum; tapioca starch; TEA-alginate; TEA-carbomer; TEA-hydrochloride; trideceth-2 carboxamide MEA; tridecyl alcohol; triethylene glycol dibenzoate; trimethyl pentanol hydroxyethyl ether; *triticum vulgare* (wheat) germ powder; *triticum vulgare* (wheat) kernel flour; *triticum vulgare* (wheat) starch; tromethamine acrylates/acrylonitrogens copolymer; tromethamine magnesium aluminum silicate; undecyl alcohol; undecylenamide DEA; undecylenamide MEA; undecylenamidopropyl betaine; welan gum; wheat germamide DEA; wheat germamidopropyl betaine; xanthan gum; yeast beta-glucan; yeast polysaccharides; *zea mays* (corn) starch; and blends thereof.

Also suitable as thickeners and/or viscosifiers are the following commercial products:

(1) Aqualon™ carboxymethylcellulose, Benecel™ methylcellulose and hydroxypropyl methylcellulose, Blanose™ sodium carboxymethylcellulose, Klucel™ hydroxypropylcellulose, Natrosol™ hydroxyethylcellulose, Natrosol™ Plus and PolySurf™ cetyl modified hydroxyethylcellulose, N-Hance™ cationic guar, N-Hance™ HP Series hydroxypropyl guar, N-Hance™ SP-100 conditioning polymer, and Supercol™ guar gum from Ashland Inc.

(2) Carbopol® Polymers, Fixate™ PLUS Polymer, Glucamate™ Thickeners, Amidex™ Surfactants, Chembetaine™ Surfactants, Chemoxide™ Surfactants, Chemonic™ Surfactants, Chemecinate™ Surfactants, Amidex™ BC-24 Surfactant, Chemoryl™ LB-30 Surfactant, Novethix™ L-10 Polymer, Ceralan™ Lanolin Product, Pemulen™ TR-1 Polymeric Emulsifier, Pemulen™ TR-2 Polymeric Emulsifier, Hydramol™ PGPD Ester, Schercodine™ M Amido-Amine, Schercodine™ P Amido-Amine, Schercomid™ Diethanolamides from The Lubrizol Corporation.

(3) Salcare® and Luvigel® from BASF Corporation.

(4) Aculyn™ 22, Aculyn™ 28, Aculyn™ 33, Aculyn™ 38, and Aculyn™ 44 from The Dow Chemical Company.

(5) Ammonyx® C and Stepan-Mild® GCC from Stepan Company.

Also suitable as a thickener/rheology modifier are lightly- to moderately-crosslinked polyvinylpyrrolidones. Disclosures of these polymers are provided in the following publications, each of which is hereby incorporated in its entirety by reference: U.S. Pat. Nos. 5,073,614; 5,312,619; 5,139,770; 5,716,634; 5,470,884; 5,759,524; 5,997,887; 6,024,942; as well as international application PCT/US10/26973, PCT/US10/26976, PCT/US10/26940, PCT/US11/32993, and PCT/US11/34515.

Personal care compositions may comprise natural extracts and/or natural products. Extensive details on natural products that can be used in personal care compositions is provided in book chapter "Chemistry of Cosmetics, Comprehensive Natural Products II" in *Chemistry and Biology*; volume 3, 2010.

Oral Care Composition Ingredients

Oral care compositions may optionally contain one or more additional ingredients. Non-limiting examples of suitable ingredients include: carriers, dentifrices, cleaning agents, breath freshening actives, pain relievers, anesthetics, anti-inflammatory agents, antimicrobial agents, antibacterial agents, anti-calculus agents, anti-plaque agents, gums, thickeners, gelling agents, surfactants, flavors, warming or tingling agents, tooth bleaching agents, whiteners, stain removers, stain preventers, abrasives, adhesives, colors, emollients, emulsifiers, preservatives, solvents, binders, stimulants, depressants, diet aids, smoking cessation aides, vitamins, minerals, throat-soothing agents, spices, herbs, herbal extracts, alkaloids (such as caffeine and nicotine), and humectants.

The choice of a carrier to be used is basically determined by the way the composition is to be introduced into the oral cavity. Carrier materials for toothpaste, tooth gel or the like include abrasive materials, sudsing agents, binders, humectants, flavoring and sweetening agents, as disclosed in e.g., U.S. Pat. No. 3,988,433. Carrier materials for biphasic dentifrice formulations are disclosed in U.S. Pat. Nos. 5,213,790; 5,145,666; 5,281,410; 4,849,213; and 4,528,180. Mouthwash, rinse or mouth spray carrier materials typically include water, flavoring and sweetening agents, etc., as disclosed in, e.g., U.S. Pat. No. 3,988,433. Lozenge carrier materials typically include a candy base; chewing gum carrier materials include a gum base, flavoring and sweetening agents, as in, e.g., U.S. Pat. No. 4,083,955. Sachet carrier materials typically include a sachet bag, flavoring and sweetening agents. For sub-gingival gels used for delivery of actives into the periodontal pockets or around the periodontal pockets, a "sub-gingival gel carrier" is chosen as disclosed in, e.g., U.S. Pat. Nos. 5,198,220 and 5,242,910. The selection of a carrier will depend on secondary considerations like taste, cost, and shelf stability, and other factors.

Oral care compositions may comprise one or more dental abrasives. Dental abrasives useful in the compositions include many different materials. The material selected must be one which is compatible within the composition of interest and does not excessively abrade dentin.

Non-limiting examples of suitable abrasives include: silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, resinous abrasive materials such as particulate condensation products of urea and formaldehyde, and blends thereof.

Another class of abrasives is the particulate thermosetting polymerized resins as described in U.S. Pat. No. 3,070,510.

Non-limiting examples of suitable resins include: melamines, phenolics, ureas, melamine-ureas, melamine-formaldehydes, urea-formaldehyde, melamine-urea-formaldehydes, cross-linked epoxides, cross-linked polyesters, and blends thereof.

Silica dental abrasives of various types may be employed because of their unique benefits of exceptional dental cleaning and polishing performance without unduly abrading tooth enamel or dentine. The silica abrasive polishing materials herein, as well as other abrasives, generally have an average particle size ranging from about 0.1 to about 30 microns, and particularly from about 5 to about 15 microns. The abrasive can be precipitated silica or silica gels such as the silica xerogels described in U.S. Pat. Nos. 3,538,230, and 3,862,307.

Non-limiting examples of suitable silica abrasives include: silica xerogels marketed under the trade name "Syloid" by the W.R. Grace & Company, Davison Chemical Division and precipitated silica materials such as those marketed by the J.M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the present invention are described in more detail in U.S. Pat. Nos. 4,340,583; 5,603,920; 5,589,160; 5,658,553; 5,651,958; and 6,740,311. Each of these disclosures is hereby incorporated in its entirety by reference.

Mixtures of abrasives can be used such as mixtures of the various grades of Zeodent® silica abrasives listed above.

The total amount of abrasive(s) in the oral care compositions typically range from about 6% to about 70% by weight; toothpastes may contain from about 10% to about 50% of abrasives by weight of the composition. Dental solution, mouth spray, mouthwash and non-abrasive gel compositions typically contain little or no abrasives.

Oral care compositions may comprise polymeric mineral surface active agent(s) (PMSAs). PMSAs include any agent which will have a strong affinity for the tooth surface, deposit a polymer layer or coating on the tooth surface and produce the desired surface modification effects. The "mineral" descriptor is intended to convey that the surface activity or substantivity of the polymer is toward mineral surfaces such as calcium phosphate minerals or teeth.

Non-limiting examples of suitable PMSAs include: polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), polypropylene glycol), poly(vinyl acetate), poly(vinyl benzyl chloride), polycarboxylates, carboxy-substituted polymers, and blends thereof. Also suitable as polymeric mineral surface active agents are the carboxy-substituted alcohol polymers described in U.S. Pat. Nos. 5,292,501; 5,213,789, 5,093,170; 5,009,882; and 4,939,284; and the diphosphonate-derivatized polymers in U.S. Pat. No. 5,011,913; the synthetic anionic polymers including polyacrylates and copolymers of maleic anhydride or acid and methyl vinyl ether (e.g., Gantrez®, as described, for example, in U.S. Pat. No. 4,627,977. Another example of a polymeric mineral surface active agent is a diphosphonate modified polyacrylic acid.

Polymers with activity must have sufficient surface binding propensity to desorb pellicle proteins and remain affixed to enamel surfaces. For tooth surfaces, polymers with end or side chain phosphate or phosphonate functions may be used, although other polymers with mineral binding activity may prove effective depending upon adsorption affinity.

PMSAs are useful in the present compositions because of their stain prevention benefit. It is believed the PMSAs provide a stain prevention benefit because of their reactivity or substantivity to mineral surfaces, resulting in desorption of portions of undesirable adsorbed pellicle proteins, in particular those associated with binding color bodies that stain teeth, calculus development and attraction of undesirable microbial species. The retention of these PMSAs on teeth can also prevent stains from accruing due to disruption of binding sites of color bodies on tooth surfaces.

The ability of PMSA to bind stain promoting ingredients of oral care products such as stannous ions and cationic antimicrobials is also believed to be helpful. The PMSA will also provide tooth surface conditioning effects which produce desirable effects on surface thermodynamic properties and surface film properties, which impart improved clean feel aesthetics both during and most importantly, following rinsing or brushing. Many of these polymeric agents are also known or expected to provide tartar control benefits when applied in oral compositions, hence providing improvement in both the appearance of teeth and their tactile impression to consumers. The desired surface effects may include: 1) creating a hydrophilic tooth surface immediately after treatment; and 2) maintaining surface conditioning effects and control of pellicle film for extended periods following product use, including post brushing or rinsing and throughout more extended periods. The effect of creating an increased hydrophilic surface can be measured in terms of a relative decrease in water contact angles. The hydrophilic surface, importantly, is maintained on the tooth surface for an extended period after using the product.

Oral care compositions may comprise additional anticalculus agent(s), such as a pyrophosphate salt as a source of pyrophosphate ion.

Non-limiting examples of suitable pyrophosphate salts include: dialkali metal pyrophosphate salts, tetraalkali metal pyrophosphate salts, and mixtures thereof. Particularly, disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms may find utility.

In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, particularly from about 1.5% to about 10%, and more particularly from about 2% to about 6%. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, particularly less than about 10% of the total pyrophosphate dissolved in the composition. Tetrasodium pyrophosphate salt may be one such pyrophosphate salt in these compositions. Tetrasodium pyrophosphate may be the anhydrous salt form or the decahydrate form, or any other species stable in solid form in the oral care compositions. The salt is in its solid particle form, which may be its crystalline and/or amorphous state, with the particle size of the salt being small enough to be aesthetically acceptable and readily soluble during use. The amount of pyrophosphate salt useful in making these compositions is any tartar control effective amount, generally from about 1.5% to about 15%, particularly from about 2% to about 10%, and more particularly from about 3% to about 8% by weight of the oral care composition.

The pyrophosphate salts are described in more detail in *Kirk-Othmer Encyclopedia of Chemical Technology*, third edition, volume 17, Wiley-Interscience Publishers (1982).

Oral care compositions may comprise peroxide compounds.

Non-limiting examples of suitable peroxide compounds include: hydrogen peroxide and organic peroxides including urea peroxide, glyceryl peroxide, benzoyl peroxide, derivatives thereof, and blends thereof.

Typically, the peroxide compound can be employed in amounts so that at least about 1% by weight of the composition comprises peroxide. The peroxide compound may comprise from about 2% to about 30% by weight of the composition. More particularly, the peroxide comprises from about 3% to about 15% by weight of the composition.

A typical peroxide concentration in the composition is generally from about 2% to about 7% by weight for home use products, and from about 15% to about 20% by weight for dental professional use.

Thickening or gelling agents used in dentifrice compositions may include nonionic polyoxyethylene polyoxypropylene block copolymers. Illustrative of polyoxyethylene polyoxypropylene block copolymers useful in the practice include block copolymers having the formula $HO(C_2H_4O)_b(C_3H_6O_6)_a(C_2H_4O)_bH$ wherein a is an integer such that the hydrophobic base represented by $(C_3H_6O_6)$ has a molecular weight of about 2,750 Da to 4000 Da, b is an integer such that the hydrophilic portion (moiety) represented by $(C_2H_4O)$ constitutes from about 70% to about 80% by weight of the copolymer. Block copolymers of this composition are available commercially under the trademark Pluronic® F type.

Pluronic® F127 has a molecular weight of 4,000 Da and contains 70% of the hydrophilic polyoxyethylene moiety.

Also suitable as a thickening agent is lightly- to moderately-crosslinked PVP, described in international application PCT/US11/30642.

The thickening agents may be present in an amount from about 15% to about 50% by weight, particularly from about 25% to about 45% by weight of the composition.

Surfactants may also be included in the oral care compositions of the invention, where they may serve in solubilizing, dispersing, emulsifying and/or reducing the surface tension of the teeth in order to increase the contact between the tooth and the peroxide. The compositions may also comprise surfactants, also commonly referred to as sudsing agents. Suitable surfactants are those which are reasonably stable and foam throughout a wide pH range. Surfactants may be chosen from anionic, nonionic, amphoteric, zwitterionic, or cationic surfactants, or blends thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are non-limiting examples of anionic surfactants of this type. Many suitable anionic surfactants are disclosed in U.S. Pat. No. 3,959,458. The compositions may comprise an anionic surfactant in an amount from about 0.025% to about 9% by weight, particularly from about 0.05% to about 5% by weight, and more particularly from about 0.1% to about 1% by weight of the composition.

Non-limiting examples of suitable anionic surfactants include: sarcosinates, taurates, isethionates, sodium lauryl sulfoacetate, sodium laureth carboxylate, and sodium dodecyl benzenesulfonate. Also suitable are alkali metal or ammonium salts of surfactants such as the sodium and potassium salts of the following: lauroyl sarcosinate, myristoyl sarcosinate, palmitoyl sarcosinate, stearoyl sarcosinate, and oleoyl sarcosinate. The sarcosinate surfactant may be present in the compositions from about 0.1% to about 2.5%, particularly from about 0.5% to about 2.0% by weight of the total composition.

Non-limiting examples of suitable cationic surfactants include: derivatives of aliphatic quaternary ammonium compounds having at least one long alkyl chain containing from about 8 to about 18 carbon atoms such as lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, cetyl pyridinium fluoride, and blends thereof. Also suitable are the quaternary ammonium fluorides described in U.S. Pat. No. 3,535,421, where the quaternary ammonium fluorides have detergent properties. Certain cationic surfactants can also act as germicides in the compositions disclosed herein.

Nonionic surfactants that may be used in the compositions of the present invention include compounds produced by the condensation of alkylene oxide groups (hydrophilic in nature) with an organic hydrophobic compound which may be aliphatic or alkylaromatic in nature.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Other surfactants such as fluorinated surfactants may also be incorporated within the compositions of the invention.

Oral care compositions may comprise flavor(s).

Non-limiting examples of suitable flavors include: methyl salicylate, ethyl salicylate, methyl cinnamate, ethyl cinnamate, butyl cinnamate, ethyl butyrate, ethyl acetate, methyl anthranilate, iso-amyl acetate, iso-armyl butyrate, allyl caproate, eugenol, eucalyptol, thymol, cinnamic alcohol, cinnamic aldehyde, octanol, octanal, decanol, decanal, phenylethyl alcohol, benzyl alcohol, benzaldehyde, α-terpineol, linalool, limonene, citral, vanillin, ethyl vanillin, propenyl guaethol, maltol, ethyl maltol, heliotropin, anethole, dihydroanethole, carvone, oxanone, menthone, β-damascenone, ionone, gamma decalactone, gamma nonalactone, gamma undecalactone, 4-hydroxy-2,5-dimethyl-3(2H)-furanone, and blends thereof.

Generally suitable flavoring agents are those containing structural features and functional groups that are less prone to oxidation by peroxide. These include derivatives of flavor chemicals that are saturated or contain stable aromatic rings or ester groups.

Also suitable are flavor chemicals that may undergo some oxidation or degradation without resulting in a significant change in the flavor character or profile. The flavor chemicals, including menthol, may be provided as single or purified chemicals rather than supplied in the composition by addition of natural oils or extracts such as peppermint, spearmint, or wintergreen oils as these sources may contain other components that are relatively unstable and may degrade in the presence of peroxide. Flavoring agents are generally used in the compositions at levels of from about 0.001% to about 5% by weight of the composition.

The flavor system may typically include sweetening agent(s). Sweeteners include compounds of natural and artificial origin.

Non-limiting examples of suitable water-soluble natural sweeteners include: monosaccharides, disaccharides and polysaccharides, such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and blends thereof.

Non-limiting examples of suitable water-soluble artificial sweeteners include: soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include dipeptide based sweeteners, such as L-aspartic acid derived sweeteners, such as L-aspartyl-L-phenylalanine methyl ester (aspartame) and materials described in U.S. Pat. No. 3,492,131, L-α-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexyen)-alanine, derivatives thereof, and blends thereof. Water-soluble sweeteners derived from naturally occurring water-soluble sweeteners, such as a chlorinated derivative of ordinary sugar (sucrose), known, for example, under the product description of sucralose as well as protein based sweeteners such as thaumatoccous danielli (Thaumatin I and II) may be used. The compositions may contain sweetener(s) in an amount from about 0.1% to about 10% by weight, in particular from about 0.1% to about 1% by weight of the composition.

In addition, the flavor system may include salivating agents, warming agents, and numbing agents. These agents are present in the compositions in an amount from about 0.001% to about 10% by weight, particularly from about 0.1% to about 1% by weight of the composition.

A non-limiting example of suitable salivating agent includes Jambus® manufactured by Takasago. Non-limiting examples of suitable warming agents include capsicum and nicotinate esters such as benzyl nicotinate. Non-limiting examples of suitable numbing agents include benzocaine, lidocaine, clove bud oil, ethanol, and blends thereof.

Oral care compositions may comprise chelating agent(s).

The chelating agents may include metal solubilizing agents and metal precipitating agents. The metal solubilizing agents include a condensed pyrophosphate compound. For purposes of this invention "condensed phosphate" relates to an inorganic phosphate composition containing two or more phosphate species in a linear or cyclic pyrophosphate form. The condensed phosphate may be sodium pyrophosphate, but may also include tripolyphosphate, hexametaphosphate, cyclic condensed phosphate or other similar phosphates well known in the field. The blend may also include an organic chelating agent. The term "organic phosphate" includes phosphonic acid, di and tri phosphonoc acid compound or its salts. An example of phosphonic acid is 1-hydroxyethylidene-1,1-diphosphonic acid that is sold under the trade name of Dequest®. The blend may also include a metal precipitating chelating agent. The term "metal precipitating chelating agent" is an agent that binds to metals and causes the metal to precipitate and includes halogens such as fluoride. The chelating agents are incorporated in the oral care compositions of the present invention in an amount from about 0.1% to about 8.0% by weight, and particularly from about 0.5% to about 3.0% by weight of the composition, in a ratio of about 3:1:1 w/w organic chelating agent: condensed phosphate chelating agent: metal precipitating agent.

Another optional ingredient that may be used in oral care compositions is a humectant. For example, a humectant may be added to keep toothpaste compositions from hardening upon exposure to air, to give compositions a moist feel to the mouth, and, for particular humectants, to impart desirable sweetness of flavor to toothpaste compositions. The humectant, on a pure humectant basis, is generally present from about 0% to about 70%, particularly from about 5% to about 25% by weight of the composition.

Non-limiting examples of suitable humectants include: edible polyhydric alcohols such as glycerin, sorbitol, xylitol, butylene glycol, polyethylene glycol, propylene glycol, trimethyl glycine, and blends thereof.

The invention also contemplates oral care compositions comprising polymer(s) described herein complexed with hydrogen peroxide. A description of such complexes is present in international application WO 91/07184, the contents of which are hereby incorporated in their entirety by reference.

Also contemplated are oral care compositions such as those described in the following patents and patent applications, the contents of each are hereby incorporated in their entirety by reference: WO 2011/068514, WO 2011/053877, US 2010/0275394, US 2011/0076090, US 2008/091935, US 2008/0181716, US 2008/0014224, WO 2007/066837, US 2008/0292669, US 2007/0071696, US 2007/0154863, US 2008/0317797, US 2005/0249678, US 2007/0178055, US 2007/0189983, WO 2005/041910, U.S. Pat. No. 7,785,572, WO 1998/005749, WO 1997/022651, and U.S. Pat. No. 5,310,563.

Oral care compositions may comprise one or more denture adhesives.

Synthetic materials presently dominate the denture adhesive market. Such materials may consist of mixtures of the salts of short-acting polymers (e.g., carboxymethylcellulose, CMC) and long-acting polymers [e.g., poly(vinyl methyl ether-co-maleic anhydride), or Gantrez® and its salts]. Polyvinylpyrrolidone (povidone) may also be used.

Other components of denture adhesive products impart particular physical attributes to the formulations. Petrolatum, mineral oil, and polyethylene oxide may be included in creams to bind the materials and to make their placement easier. Silicon dioxide and calcium stearate may be used in powders to minimize clumping. Menthol and peppermint oils may be used for flavoring, red dye for color, and sodium borate and methyl- or poly-paraben as preservatives.

The synthesis of the modified natural compounds can be prepared according to the Examples set out below. The examples are presented for purposes of demonstrating, but not limiting, the preparation of the compounds and compositions of this invention.

EXAMPLES

Example 1

1 Molar Eq. ESO Opened with 3.0 Molar Eq. HEP

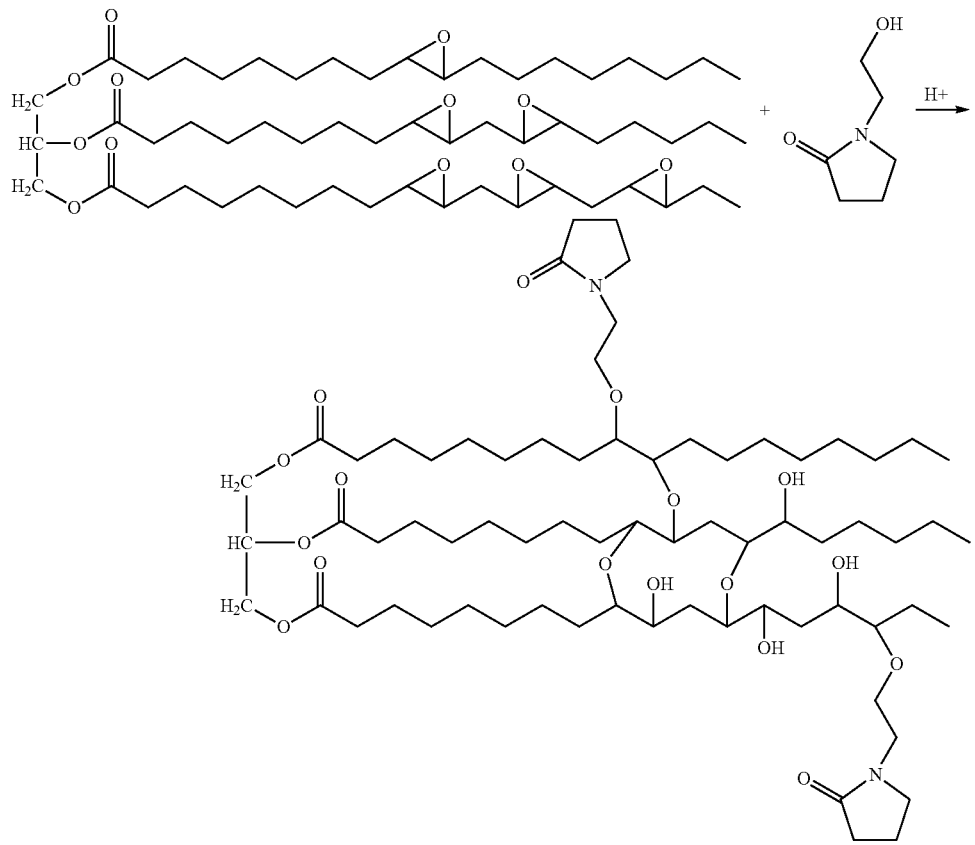

Note:
This scheme is intended to be illustrate the reaction chemistry and a possible product. Due to the multiplicity of reaction sites and reactants, and the structure may not be the only description possible.

A 500 mL, 4-neck, round-bottom flask was fitted with a mechanical mixer, oil bath with temperature controller, thermometer and bubbler gas outlet. The flask was charged with 9.7 g (0.075 mol.) hydroxyethyl pyrrolidone (HEP) and 1.0 mL tetrafluoroboric acid catalyst (50% aqueous solution). Mixing and heating of the reaction in the hot oil bath (set point=115° C.) was initiated. Epoxidized soybean oil (ESO) (Paraplex® G-60; The Hallstar Company; Chicago, Ill.) (28.83 g, 0.025 mol.) was added over 30 minutes in three shots: 10.0 g at t=0 minutes at a temperature of about 98° C., 9.0 g at t=15 minutes, and 10.0 g at t=30 minutes. The reaction was monitored for HEP level by GC (13.6 min) and epoxide ring depletion was detected by FT-IR (825-835 cm$^{-1}$). The reaction was completed 10.5 hours following the third ESO addition. The crude reaction product, a clear, amber-gold oil, was cooled to room temperature, and then dichloromethane or ethyl acetate (250 mL) was added with mixing to dissolve the viscous oil. The resulting clear gold solution was transferred to a 1-L, 4-neck, round-bottom flask. The pH of reaction solution and water (1/1 v/v) was found to be about 4. The reaction solution (about 265 mL) was filtered through a pad of 110 g of potassium bicarbonate charged to a small Buchner funnel, followed by a 100 mL dichloromethane (or ethyl acetate) rinse of the salts. This filtration step was repeated two more times, after which the reaction solution pH measured 6.0. On this scale, the final reaction solution volume was about 425 mL. Then the reaction solution was washed three times with 425 mL water (each wash). Each time, 100 mL brine was added to hasten emulsions/dispersions phase separation and removal, which required about 0.5 hour each. A cloudy gold organic phase was collected, and about 50 g magnesium sulfate was added and mixed for 0.5 hour to dehydrate the mixture. Additional magnesium sulfate was added as needed. The reaction mixture was filtered, yielding a clear solution having a deep-gold color. The solvent was removed via a rotary evaporator over 2.75 hours at 50° C. and 40 Torr, resulting in about 16 g of viscous clear amber oil. The pH of product and water measured to be about 7. The chemical structure shown above was confirmed by FT-IR and NMR analyses, and NMR results indicated that all epoxy rings were open. HEP was incorporated into the product at 0.69 equivalent HEP per 1.00 equivalent of ESO. In addition to ether linkages between the soybean oil and HEP, inter- and intramolecular ether linkages also may exist in the product.

The modified soybean oil had the appearance of a deep amber liquid with a Brookfield viscosity of 43,000 cP. Its solubility/dispersibility behavior was evaluated at 5% (w/w) addition level with the following results: water-milky dispersion; ethanol-clear solution; 2-propanol-clear solution. Without being bound by theory, the use of aqueous tetrafluoroboric acid is believed to help contribute to the water dispersibility of this modified soybean oil. One skilled in the art can produce related modified natural compounds with higher or lower addition levels of HEP, thereby modulating these solubility/dispersibility results even further.

Example 2

1 Molar Eq. ESO Opened with 2 Molar Eq. HEP plete 10.5 hours after the third ESO addition. The crude reaction product, a clear, amber-gold oil, was cooled to room temperature, and then dichloromethane or ethyl acetate (250 mL) was added with mixing to dissolve the viscous oil. Potassium bicarbonate (100 g) was added to the clear, amber-gold reaction solution, the mixture was mixed for at least one hour, and then filtered and rinsed with solvent. The volume of the hazy, gold reaction solution at this point was about 350 mL. A small sample of the reaction solution plus

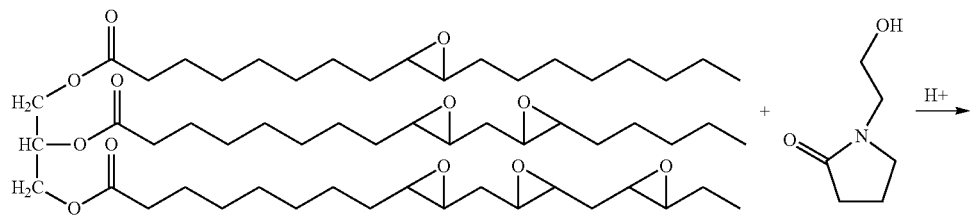

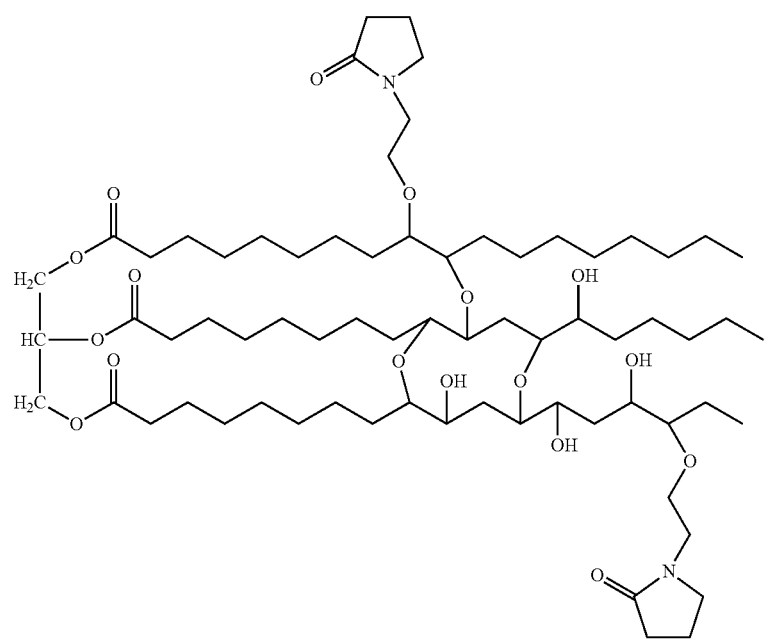

Note:
This scheme is intended to be illustrate the reaction chemistry and a possible product. Due to the multiplicity of reaction sites and reactants, and the structure may not be the only description possible.

A 1000 mL, 4-neck, round-bottom flask was fitted with a mechanical mixer, oil bath with temperature controller, thermometer and bubbler gas outlet. The flask was charged with epoxidized soybean oil (ESO) (Paraplee G-60; The Hallstar Company; Chicago, Ill.) (28.83 g, 0.025 mol.). Mixing and heating of the reaction in the hot oil bath (set point=112° C.) was initiated. A quantity of 6.46 g (0.05 mol) of hydroxyethyl pyrrolidone (HEP) and 1.0 mL tetrafluoroboric acid catalyst were combined and added in three equal amounts after t=0, 10, and 15 minutes at about 98° C. reaction temperature. The reaction was monitored for HEP level by GC (13.6 min) and epoxide ring depletion was detected by FT-IR (825-835 cm$^{-1}$). Then, 1 mL of tetrafluoroboric acid was added 4 hours after the third HEP/tetrafluoroboric acid addition. The reaction was considered com-water (1/1 v/v) formed a white emulsion having a pH of about 8. Then the reaction solution was washed three times with 250 mL water (each wash). Each time, 100 mL brine was added to hasten emulsions/dispersions phase separation and removal, which required between 1 to 4 hours each. A cloudy, gold organic phase was collected, and 50 g magnesium sulfate was added and mixed for 1 hour to dehydrate the mixture. Additional magnesium sulfate was added as needed. The reaction mixture was filtered, yielding a clear deep-gold solution. The solvent was removed via a rotary evaporator at 50° C. and 25 Torr, resulting in about 22.4 g of a viscous, clear, gold viscous oil. The pH of product in water was measured to be about 7. The chemical structure shown above was confirmed by FT-IR and NMR analyses, and NMR results indicated that all epoxy rings were open.

HEP was incorporated into the product at 0.30 equivalent HEP per 1.00 equivalent of ESO. In addition to ether linkages between the soybean oil and HEP, inter- and intramolecular ether linkages also may exist in the product.

Example 3

1 Molar Eq. ESO Opened with 3 Molar Eq. HEP in Toluene

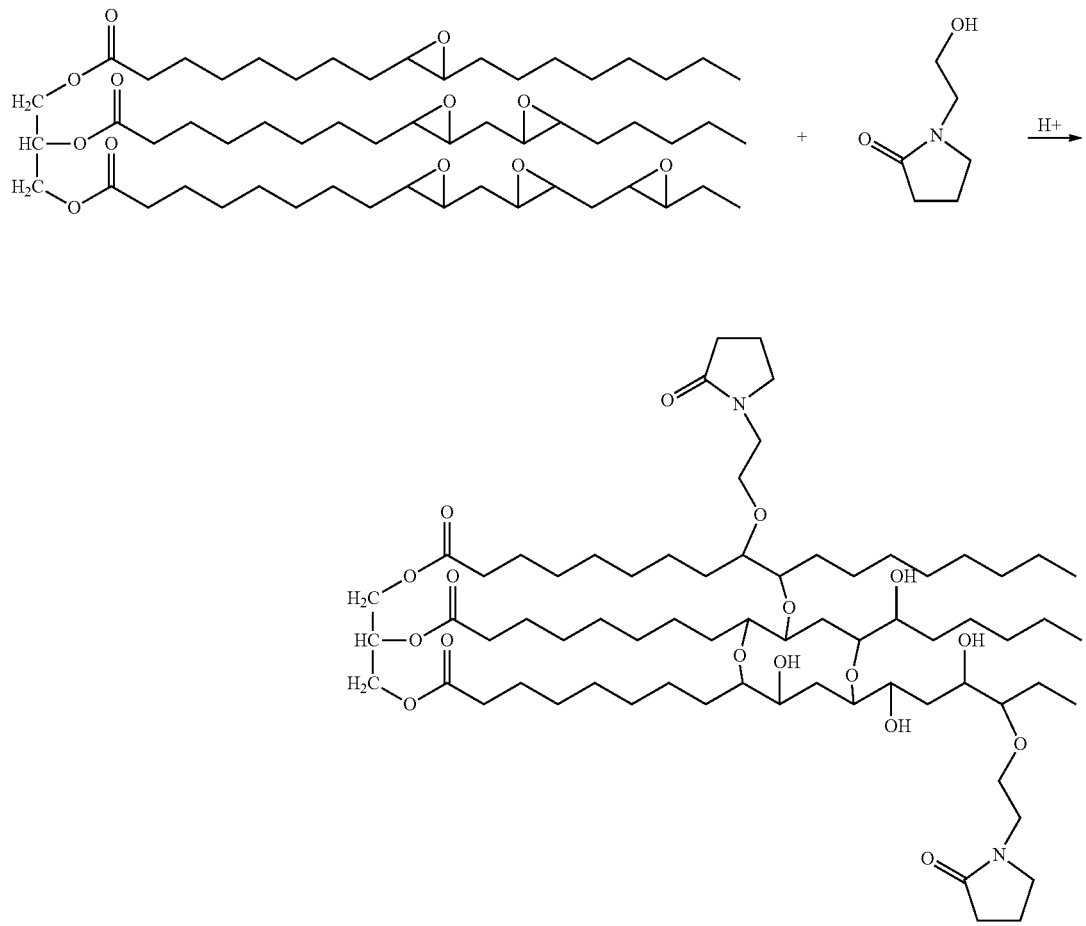

Note:
This scheme is intended to be illustrate the reaction chemistry and a possible product.
Due to the multiplicity of reaction sites and reactants, and the structure may not be the only description possible.

A 500 mL, 4-neck, round-bottom flask was fitted with a mechanical mixer, oil bath with controller, thermometer and reflux condenser. The flask was charged with epoxidized soybean oil (ESO) (Paraplex® G-60; The Hallstar Company; Chicago, Ill.) (29.0 g, 0.025 mol) dissolved in 90.0 g of toluene. In this Example the reaction was performed in refluxing toluene. Mixing and heating of the solution in the hot oil bath (set point=140° C.) were initiated. Hydroxyethyl pyrrolidone (HEP) (9.7 g, 0.0500 mol) and 1.0 mL tetrafluoroboric acid catalyst were combined, and added over 15 minutes in three equal amount at t=0, 10, and 15 minutes at about 98° C. reaction temperature. The reaction samples were monitored for HEP level by GC (13.6 min.) and epoxide ring depletion was detected by FT-IR (825-835 $cm^{-1}$). A second 1.0 mL of tetrafluoroboric acid was added 4 hours after the third HEP/tetrafluoroboric acid addition.

The reaction was considered complete 22 hours following the third ESO addition. The crude reaction product was a clear, amber-gold oil with a pH of 4. Potassium bicarbonate (100.0 g) was added, the resulting gold slurry was mixed for 70 minutes, and then the gold mixture was filtered to remove salts. The salts were rinsed and the reaction solution volume was adjusted to 400 mL. The reaction solution was then washed three times with 400 mL water (each wash). Each time, 100 mL brine was added to hasten emulsions/dispersions phase separation and removal, and extra brine was added as needed. GC analysis revealed the HEP was removed by the water washings, and the aqueous-phase pH was about 7-8. The top, cloudy gold phase (increased to 400 mL volume) was collected and about 50 g of magnesium sulfate was added and mixed for about 0.5 hour to dry. The mixture was filtered to yield a clear, deep gold solution. Solvent was removed via rotary evaporation for 2.75 hours at 60° C. and about 20 Torr, resulting in 23 g of a clear, amber viscous oil having a pH of about 7.0. The chemical structure shown above was confirmed by FT-IR and NMR analyses, and NMR results indicated that all epoxy rings were open. REP was incorporated into the product at 0.85 equivalent HEP per 1.00 equivalent of ESO. In addition to ether linkages between the soybean oil and HEP, inter- and intramolecular ether linkages also may exist in the product.

Example 4

1 Molar Eq. ESO Opened with 3 Molar Eq. PEG-ME

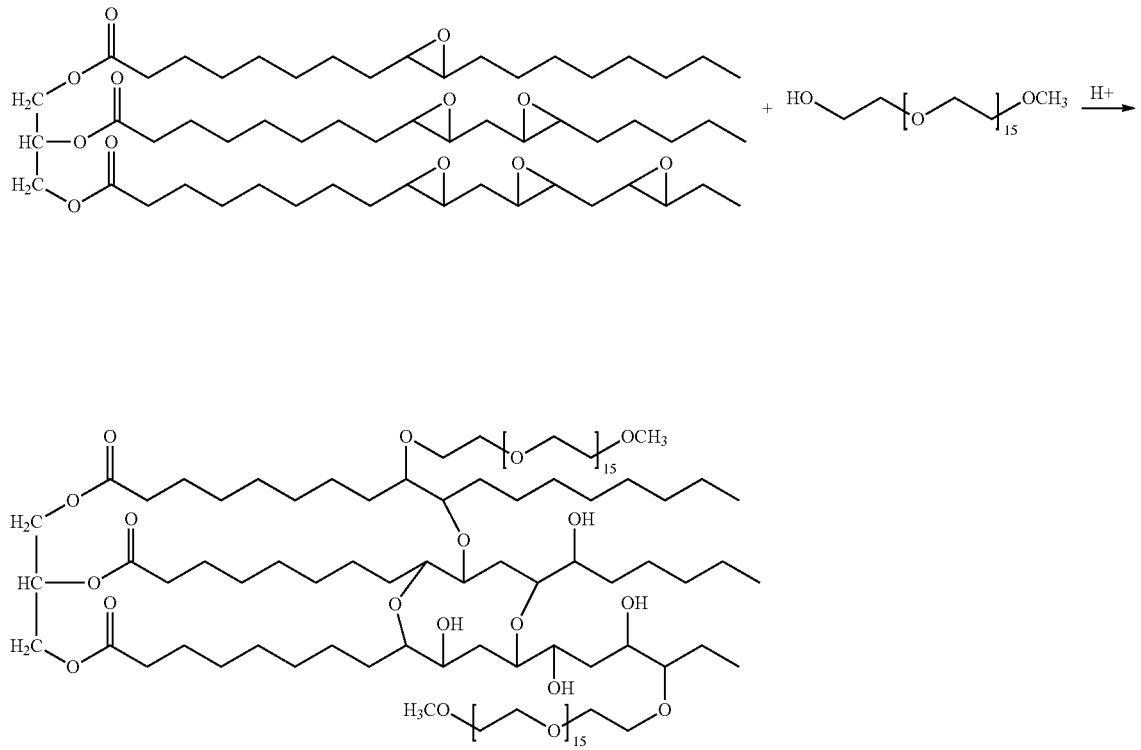

Note:
This scheme is intended to be illustrate the reaction chemistry and a possible product. Due to the multiplicity of reaction sites and reactants, and the structure may not be the only description possible.

A 500 mL, 4-neck, round-bottom flask was fitted with a mechanical mixer, oil bath with controller, thermometer and reflux condenser. The reaction flask was charged with 41.25 g (0.075 mol.) of polyethylene glycol methyl ether (PEG-ME) having an average molecular weight of 550 Da (Carbowax™ MPEG 550; The Dow Chemical Company, Midland, Mich.), and 1.0 mL of tetrafluoroboric acid catalyst. Mixing and heating of the flask in the hot oil bath (set point=115° C.) was initiated. Epoxidized soybean oil (ESO) (Paraplex® G-60; The Hallstar Company; Chicago, Ill.) (29.0 g, 0.025 mol) was added over 30 minutes in about three equal shots at t=0, 15, and 30 minutes at about 98° C. reaction temperature. The reaction was monitored for epoxy ring depletion using FT-IR (825-835 $cm^{-1}$). Heating was stopped after 10.5 hours following the third ESO addition. The crude reaction product was a clear, amber-gold oil, and NMR analysis determined all expoxide rings were open (closed rings were not detected). The cooled reaction product was blended with 250 mL ethyl acetate (or dichloromethane) to dissolve the viscous oil. The pH of the reaction solution plus water (1/1 v/v) was found to be about 4. The reaction solution (about 265 mL) was filtered through a pad of 110 g of potassium bicarbonate charged to a small Buchner funnel, followed by a 100 mL solvent rinse of the salts. This neutralization treatment was repeated two more times, and the final aqueous phase pH was found to be 7.0. On this scale, the final reaction solution volume was about 500 mL. Then, the reaction solution was washed two times with 500 mL water (each wash), and each time 400 in L brine was added to remove emulsions/dispersions. The time required for removal time ranged from 1-2 hours to overnight. The aqueous phase was discarded, and a cloudy, organic phase with a gold color was collected. The organic phase was increased, when necessary to at least 400 mL, and about 50 g if magnesium sulfate was added with mixing to dehydrate the mixture, and was filtered to yield a clear, deep gold solution. Solvent was removed at 60° C. by rotary evaporation for 1.5 hours at less than 20 Torr. About 23 g of a viscous, dark amber oil was collected. The chemical structure shown above was confirmed by FT-IR and NMR analyses, and NMR results indicated that all epoxy rings were open. PEG-ME was incorporated into the product at 0.96 equivalent per 1.00 equivalent of ESO. In addition to ether linkages between the soybean oil and PEG-ME, inter- and intramolecular ether linkages also may exist in the product.

The modified soybean oil had the appearance of a deep amber liquid with a Brookfield viscosity of 3,400 cP. Its solubility was evaluated at 5% (w/w) addition level with the following results: water, clear solution; ethanol, clear solution; 2-propanol, clear solution. Without being bound by theory, the use of aqueous tetrafluoroboric acid is believed to help contribute to the water solubility of this modified soybean oil. One skilled in the art can produce related modified natural compounds with higher or lower addition

Example 5

1 Molar Eq. ESO Opened with 1.5 Molar Eq. PEG-ME and 1.5 Molar Eq. HEP

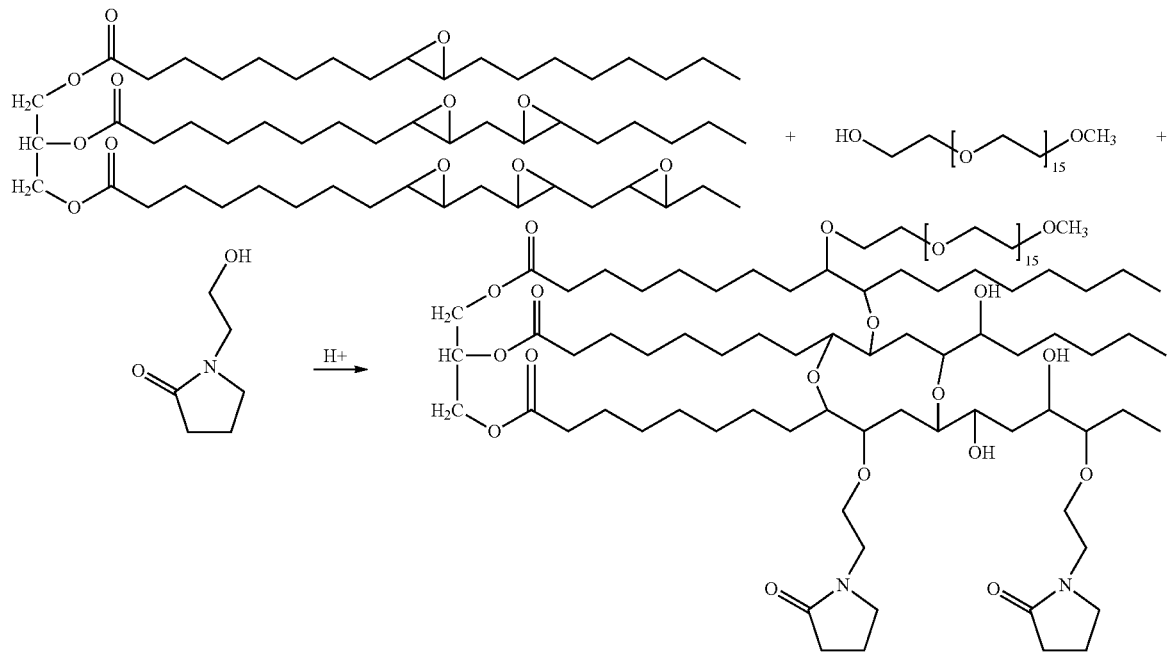

Note:
This scheme is intended to be illustrate the reaction chemistry and a possible product.
Due to the multiplicity of reaction sites and reactants, and the structure may not be the only description possible.

A 500 mL, 4-neck, round-bottom flask was fitted with a mechanical mixer, oil bath with controller, thermometer, and gas outlet. The flask was charged with 20.625 g (0.0375 mol) of polyethylene glycol methyl ether (PEG-ME) having an average molecular weight of 550 Da (Carbowax™ MPEG 550; The Dow Chemical Company, Midland, Mich.), 4.84 g (0.0375 mol) of hydroxyethyl pyrrolidone (HEP), and 1.0 mL of tetrafluoroboric acid catalyst. Mixing and heating of the flask in the hot oil bath (set point=110° C.) was initiated. Epoxidized soybean oil (ESO) (Paraplex® G-60; The Hallstar Company; Chicago, Ill.) (29.0 g, 0.025 mol) was added over 30 minutes in three almost equal amounts at t=0, 15, and 30 minutes at about 98° C. reaction temperature. Heating and mixing were continued after the ESO additions. The reaction was monitored via epoxy ring depletion using FT-IR (825-835 cm$^{-1}$), and preliminary NMR measurements suggested some epoxy rings were still closed. Consequently, another 1.0 mL of the tetrafluoroboric acid catalyst was added, and the reaction was continued for a total of 12.5 hours following the third ESO addition. The crude reaction product was a viscous, amber-colored oil. The cooled product was blended with 250 mL of ethyl acetate (or dichloromethane) and mixed for 15 minutes to dissolve the viscous oil. The pH of the reaction solution plus water (1/1 v/v) was found to be about 1-2. The reaction solution (about 295 mL) was filtered through a pad of 110 g of potassium bicarbonate charged to a small Buchner funnel, followed by a 100 mL solvent rinse of the salts. This neutralization treatment was repeated two more times. The final product pH was 7.5, and the reaction solution volume was about 425 mL. Then the reaction solution was washed three times with 250 mL water (each wash), and with each rinse 100 mL brine was added to remove emulsions/dispersions. More brine was added (300 mL total) with the third wash, after which the aqueous pH ranged between 7 and 8. Finally, the aqueous phase was discarded, and a foamy, cloudy, gold-colored organic phase (pH of 8, on top if ethyl acetate, on bottom if dichloromethane) was collected. The organic phase was adjusted to at least 400 mL volume, and about 50 g (or more) of sodium sulfate was added to dehydrate the mixture. The blend was mixed for 0.5 hour and filtered to yield a deep, gold-colored solution. Solvent was removed at 60° C. by rotary evaporation for 2.0 hours at less than 20 Torr. About 20 g of clear, amber-colored viscous oil was collected. The pH of the oil product dispersed in water ranged between 7.5 and 8.0. PEG-ME and HEP were incorporated into the oil at a ratio of 1.00 equivalent ESO:0.3 equivalent PEG-ME:0.6 equivalent HEP. The chemical structure shown above was confirmed by FT-IR and NMR analyses, and NMR results indicated that all epoxy rings were open. In addition to ether linkages between the soybean oil and PEG-ME, and between soybean oil and HEP, inter- and intramolecular ether linkages also may exist in the product.

The modified soybean oil had the appearance of a deep amber liquid with a Brookfield viscosity of 19,000 cP. Its solubility was evaluated at 5% (w/w) addition level with the following results: water, milky dispersion; ethanol, clear solution; 2-propanol, clear solution. Without being bound by theory, the use of aqueous tetrafluoroboric acid is believed to help contribute to the water dispersibility of this modified soybean oil. One skilled in the art can produce related modified natural compounds with higher or lower addition levels of PEG-ME, thereby modulating these solubility/dispersibility results even further.

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

We claim:

1. A modified natural compound produced from a reaction of:
   (A) at least one of an epoxidized natural fatty acid, a maleated natural fatty acid, an epoxidized natural oil, a maleated natural oil, or a combination thereof; and
   (B) at least one lactam comprising a hydroxyl functional group, wherein the hydroxyl-containing lactam has the structure:

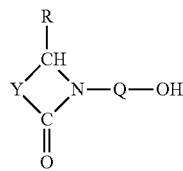

wherein:
   Y is an alkylene or alkenylene group comprising 2 to 50 carbon atoms, wherein 2 to 4 carbon atoms reside in the lactam ring between the

group and the

group;
   Q is selected from the group consisting of a functionalized and unfunctionalized alkylene of linear, branched, or cyclic structure, an arylene, and combinations thereof, wherein any of the before mentioned groups may be with or without oxygen atom(s); and
   R is selected from the group consisting of hydrogen, functionalized and unfunctionalized alkyl, cycloalkyl, alkenyl, and aryl groups, wherein any of the groups may be with or without heteroatoms, and wherein the lactam of the at least one lactam remains a lactam in the modified natural compound.

2. The modified natural compound according to claim 1, wherein the epoxidized natural oil is selected from the group consisting of an epoxidized avocado oil, an epoxidized coconut oil, an epoxidized corn oil, an epoxidized cottonseed oil, an epoxidized jojoba oil, an epoxidized linseed oil, an epoxidized nut oil, an epoxidized olive oil, an epoxidized palm oil, an epoxidized raisin oil, an epoxidized rapeseed oil, an epoxidized safflower oil, an epoxidized sesame oil, an epoxidized soybean oil, an epoxidized squash oil, an epoxidized sunflowers oil, and combinations thereof; and the maleated natural oil is selected from the group consisting of a maleated avocado oil, a maleated coconut oil, a maleated corn oil, a maleated cottonseed oil, a maleated jojoba oil, a maleated linseed oil, a maleated nut oil, a maleated olive oil, a maleated palm oil, a maleated raisin oil, a maleated rapeseed oil, a maleated safflower oil, a maleated sesame oil, a maleated soybean oil, a maleated squash oil, a maleated sunflowers oil, and combinations thereof.

3. The modified natural compound according to claim 1, wherein the (B) lactam having at least one hydroxyl functional group is selected from the group consisting of:

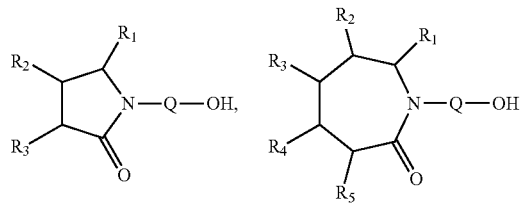

and combinations thereof, wherein: each $R_1$, $R_2$, $R_3$, $R_4$, and $R_5$ is independently selected from the group consisting of hydrogen, functionalized and unfunctionalized cycloalkyl, alkenyl, and aryl groups, wherein any of the groups may be with or without heteroatoms.

4. A modified natural compound produced from the reaction of:
   (A) at least one epoxidized natural fatty acid, maleated natural fatty acid, epoxidized natural oil, maleated natural oil, or blend thereof;
   (B) at least one lactam having at least one hydroxyl functional group, wherein the hydroxy-containing lactam has the structure:

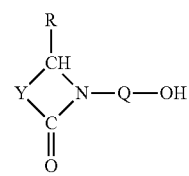

wherein:
   Y is an alkylene or alkenylene group comprising 2 to 50 carbon atoms, wherein 2 to 4 carbon atoms reside in the lactam ring between the

group and the

group;
Q is selected from the group consisting of functionalized and unfunctionalized alkylene of linear, branched, or cyclic structure, arylene, and combinations thereof, wherein any of the before mentioned groups may be with or without oxygen atom(s); and
R is selected from the group consisting of hydrogen, functionalized and unfunctionalized alkyl, cycloalkyl, alkenyl, and aryl groups, wherein any of the groups may be with or without heteroatoms; and
(C) at least one alcohol.

5. The modified natural compound according to claim 4, wherein the alcohol is selected from the group consisting of: monohydric alcohols, polyhydric alcohols, unsaturated aliphatic alcohols, alicyclic alcohols, and combinations thereof.

6. The modified natural compound according to claim 5, wherein said monohydric alcohol is selected from the group consisting of: methanol, ethanol, menthol, polyethylene glycol methyl ether, 1-propanol, 2-propanol, 1-butanol, 2-butanol, amyl alcohol, cetyl alcohol, benzyl alcohol, hydroxymethyl (meth)acrylate, hydroxyethyl (meth)acrylate and combinations thereof.

7. The modified natural compound according to claim 5 wherein said polyhydric alcohol is selected from the group consisting of: ethylene glycol, polyethylene glycols, propylene glycol, polypropylene glycols, butylene glycol, polybutylene glycols, 1,3-propanediol, 1,4-butane diol, 1,5-pentanediol, 1,6-hexanediol, methoxypolyethylene glycols, glycerin, erythritol, mannitol, xylitol, monosaccharides, glucose, polysaccharides, starch, cellulose, hydroxyethylcellulose, hydroxypropylcellulose, cyclodextrins, glyco-proteins, polymeric alcohols, polyvinyl alcohol, polyhydroxymethyl (meth)acrylate, polyhydroxyethyl (meth)acrylate, and combinations thereof.

8. The modified natural compound according to claim 1, wherein the modified natural compound is soluble in an organic alcohol.

9. The modified natural compound according to claim 8, wherein the solubility of the modified natural compound in the organic alcohol is at least 5% (w/w).

10. The modified natural compound according to claim 1, wherein the modified natural compound is selected from the group consisting of:
a. epoxidized soybean oil reacted with hydroxyethyl pyrrolidone, wherein the epoxide functional groups are partially or fully opened;
b. maleated soybean oil reacted with hydroxyethyl pyrrolidone, wherein the product contains unreacted anhydride groups; and
c. combinations of natural compounds that are disclosed in (a) to (b).

11. The modified natural compound according to claim 4, wherein the natural compound is selected from the group consisting of:
a. epoxidized soybean oil reacted with hydroxyethyl pyrrolidone and methanol, wherein the epoxide functional groups are partially or fully opened;
b. epoxidized soybean oil reacted with hydroxyethyl pyrrolidone and polyethylene glycol, wherein the epoxide functional groups are partially or fully opened; and
c. epoxidized soybean oil reacted with hydroxyethyl pyrrolidone, polyethylene glycol methyl ether, and methanol, wherein the epoxide functional groups are partially or fully opened;

d. maleated soybean oil reacted with hydroxyethyl pyrrolidone and methanol, wherein the product contains unreacted anhydride groups;
e. maleated soybean oil reacted with hydroxyethyl pyrrolidone and polyethylene glycol methyl ether, wherein the product contains unreacted anhydride groups; and
f. maleated soybean oil reacted with hydroxyethyl pyrrolidone, polyethylene glycol methyl ether, and methanol, wherein the product contains unreacted anhydride groups; and
g. combinations of natural compounds that are disclosed in (a) to (f).

12. A composition comprising a modified natural compound produced from the reaction of:
(A) at least one of an epoxidized natural fatty acid, maleated natural fatty acid, epoxidized natural oil, maleated natural oil, or blend thereof; and
(B) at least one lactam having at least one hydroxyl functional group, wherein the hydroxy-containing lactam has the structure:

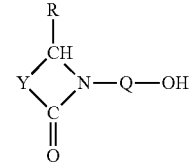

wherein:
Y is an alkylene or alkenylene group comprising 2 to 50 carbon atoms, wherein 2 to 4 carbon atoms reside in the lactam ring between the

group and the

group;
Q is selected from the group consisting of functionalized and unfunctionalized alkylene of linear, branched, or cyclic structure, arylene, and combinations thereof, wherein any of the before mentioned groups may be with or without oxygen atom(s); and
R is selected from the group consisting of hydrogen, functionalized and unfunctionalized alkyl, cycloalkyl, alkenyl, and aryl groups, wherein any of the groups may be with or without heteroatoms; and
wherein the lactam of the at least one lactam remains a lactam in the modified natural compound, and
wherein said composition is an adhesive, an aerosol, an agricultural, a beverage, a carrier system, a cleaning, a coating, a detergent, a drug, an emulsifier, an encapsulation, a food, a lithographic, a membrane, a lubricant, an oilfield, a personal care composition, a pharmaceutical/nutritional, a paint, a pigment dispersion, a solubilizer, or a stabilizer composition.

13. The personal care composition according to claim 12, wherein said personal care composition is a skin care, a color cosmetic care, a hair styling, a hair non-styling, a sun care, or an oral care composition.

14. A modified natural compound produced from a reaction of:
(A) at least one of a maleated natural fatty acid, a maleated natural oil, or a combination thereof; and
(B) at least one lactam having at least one hydroxyl functional group, wherein the hydroxyl-containing lactam has the structure:

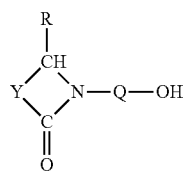

wherein:
Y is an alkylene or alkenylene group comprising 2 to 50 carbon atoms, wherein 2 to 4 carbon atoms reside in the lactam ring between the

group and the

group;
Q is selected from the group consisting of functionalized and unfunctionalized alkylene of linear, branched, or cyclic structure, arylene, and combinations thereof, wherein any of the before mentioned groups may be with or without oxygen atom(s); and
R is selected from the group consisting of hydrogen, functionalized and unfunctionalized alkyl, cycloalkyl, alkenyl, and aryl groups, wherein any of the groups may be with or without heteroatoms, and wherein the lactam of the at least one lactam remains a lactam in the modified natural compound.

15. The modified natural compound according to claim 14, wherein said (B) lactam having at least one hydroxyl functional group is selected from the group consisting of:

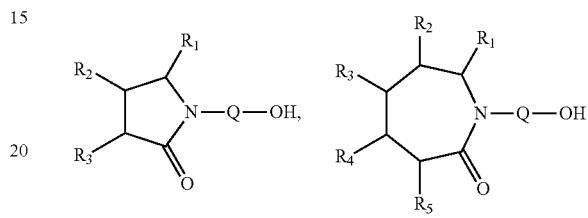

and combinations thereof, wherein: each $R_1$, $R_2$, $R_3$, $R_4$, and $R_5$ is independently selected from the group consisting of hydrogen, functionalized and unfunctionalized cycloalkyl, alkenyl, and aryl groups, wherein any of the groups may be with or without heteroatoms.

16. The modified natural compound according to claim 14, wherein the modified natural compound is soluble in an organic alcohol.

17. The modified natural compound according to claim 16, wherein the solubility of the modified natural compound in the organic alcohol is at least 5% (w/w).

18. The modified natural compound according to claim 1, wherein the modified natural compound is selected from the group consisting of a maleated soybean oil reacted with a hydroxyethyl pyrrolidone, wherein the product contains unreacted anhydride groups.

* * * * *